United States Patent [19]

Miyata et al.

[11] Patent Number: 5,849,563
[45] Date of Patent: *Dec. 15, 1998

[54] EUKARYOTES EXPRESSING SINGLE STRANDED HYBRID MOLECULES

[75] Inventors: Shohei Miyata, Saitama, Japan; Atsushi Ohshima, Highland Park, N.J.; Sumiko Inouye; Masayori Inouye, both of Bridgewater, N.J.

[73] Assignee: The University of Medecine and Dentistry of New Jersey, Newark, N.J.

[ * ] Notice: The term of this patent shall not extend beyond the expiration date of Pat. Nos. 5,405,775 and 5,436,141.

[21] Appl. No.: 507,634

[22] Filed: Jul. 25, 1995

Related U.S. Application Data

[63] Continuation-in-part of Ser. No. 753,110, Aug. 30, 1991, Pat. No. 5,436,141, which is a continuation-in-part of Ser. No. 315,427, Feb. 24, 1989, Pat. No. 5,079,151, and a continuation-in-part of Ser. No. 315,316, Feb. 24, 1989, Pat. No. 5,320,958, and a continuation-in-part of Ser. No. 315,432, Feb. 24, 1989, abandoned, and a continuation-in-part of Ser. No. 517,946, May 2, 1990, abandoned, and a continuation-in-part of Ser. No. 518,749, Mar. 2, 1990, Pat. No. 5,405,775.

[51] Int. Cl.$^6$ .................... C12N 5/10; C12N 1/15
[52] U.S. Cl. .................... 435/240.2; 435/240.4; 435/254.21; 435/320.1; 536/25.2
[58] Field of Search ............... 435/252.33, 91.1, 435/240.4, 240.2, 254.21, 320.1; 536/25.2

[56] References Cited

U.S. PATENT DOCUMENTS

| | | | |
|---|---|---|---|
| 5,405,775 | 4/1995 | Inouye et al. | 435/252.33 |
| 5,436,141 | 7/1995 | Miyata et al. | 435/91.1 |

*Primary Examiner*—James Ketter
*Attorney, Agent, or Firm*—Weiser & Associates, P.C.

[57] ABSTRACT

Eucaryotic cells like mammal and plant cells transfected with genes, called retrons, which code for stable single-stranded hybrid molecules (msDNA) containing RNA and DNA portions are disclosed. The retrons producing said linked RNA and DNA portions of the msDNAs also contain a gene encoding a reverse transcriptase (RT), which is necessary for the synthesis of the msDNAs. The msDNAs may contain foreign nucleic acid fragments which may be antisense fragments. These msDNA antisense vectors are useful for targeting genes of target proteins.

30 Claims, 17 Drawing Sheets

FIG. 8A

EUKARYOTES EXPRESSING SINGLE STRANDED HYBRID MOLECULES

RELATED PATENT APPLICATIONS

This is a continuation-in-part of allowed pending patent application Ser. No. 07/753,110, filed Aug. 30, 1991, issued on Jul. 25, 1995 as U.S. Pat. No. 5,436,141, which is in turn a continuation-in-part of Ser. No. 07/315,427 filed Feb. 24, 1989 now U.S. Pat. No. 5,079,151; 07/315,316 filed Feb. 24, 1989, now U.S. Pat. No. 5,320,958; 07/315,432 filed Feb. 24, 1989, now abandoned; 07/517,946 filed May 2, 1990, now abandoned, and 07/518,749 filed May 2, 1990, now U.S. Pat. No. 5,405,775. This application is also related to patent application Ser. No. 08/503,730, entitled: NEW HYBRID MOLECULES, filed on Jul. 18, 1995.

FIELD OF THE INVENTION

The invention relates to the field of eucaryotic cells transfected with a group of genes known as a retron for the synthesis of stable single-stranded hybrid DNA-RNA molecules. The invention also relates to new eucaryotic vectors carrying the necessary elements to produce the single-stranded DNA-RNA hybrid molecules.

BACKGROUND

Gram-negative bacteria such as *Myxococcus xanthus*, *Stigmatella aurantiaca* and *Escherichia coli* have been found to contain a retroelement called a retron. In *TIBS*, 16, 18–21 (1991a), the authors report on a peculiar type of satellite DNA, named multicopy single-stranded DNA (msDNA). These molecules are characterized by a structure which comprises a single-stranded DNA branching out of an internal guanosine residue of a single-stranded RNA molecule by a unique 2',5'-phosphodiester linkage. These molecules are thus single-stranded DNA-RNA hybrids. Reverse transcriptase is required for the synthesis of these msDNAs. In *Ann. Rev. Microbiol.*, 45, 163–186 (1991b), the authors present a comprehensive review on msDNAs. Also see msDNA in Bacteria, Lampson et al., *Progress in Nucleic Acid Research and Molecular Biology*, 60, 1–24.

The production of single-stranded cDNA by reverse transcriptase as a template is an obligatory step for RT-mediated transcription of retroelements. See *Retroelements*. See Weiner et al., *Ann. Rev. Biochem.*, 55, 631–661 (1986) for review. This includes integration of retroviruses into mammalian genomes, production of infectious retroviruses from pro-viruses integrated into genomes, retrotransposition of retroelements, and formation of pseudo genes in eucaryotic cells.

However, single-stranded cDNAs produced in vivo by RT have never been directly detected, probably because of their instability.

While the production of msDNAs in bacteria has been a most significant development, the in vivo production of single-stranded DNAs in eucaryotic cells, e.g., yeast or higher eucaryotic cells like plant and mammalian cells, is of even greater interest. Eucaryotes have well-known advantages over procaryotes for producing target molecules. There is an important need to produce stable single-stranded DNA in a sufficient yield for numerous practical uses in research and in industry. This invention has made an important contribution in that respect in producing single-stranded RNA-DNA structures which are detectable, stable and useful.

SUMMARY OF THE INVENTION

In accordance with the invention, a fundamental finding has been made. It has been discovered that single-stranded hybrid molecules containing DNA and RNA which are stable can be produced in vivo in eucaryotic cells. Any eucaryotic cell, including animal and plant cells, capable of being transfected with a competent vector, such as a plasmid, may be be used to produce the hybrid molecule. Examples of suitable eucaryotes include vertebrates, such as fishes, birds, mammals, and amphibians. Plants, both monocotyledonous and dicotyledonous plants, may be transfected to produce the hybrid molecule of the invention. Examples of suitable plants include crops of commercial importance, such as cereals such as wheat, oats, and rice, legumes such as soybeans and peas, corn, grasses such as alfalfa, and cotton.

Briefly described, the invention provides a method (or process) for producing in vivo stable, single-stranded DNAs in eucaryotic cells like yeasts or plant cells or mammalian cells. The method of the invention produces a single-stranded cDNA by means of a retroelement called a retron. The single-stranded DNA is produced as an integral part of a branched RNA-linked multicopy single-stranded DNA (msDNA) structure. These structures are stable, i.e., detectible after production and isolation in spite of the fact that they are constituted of RNA and DNA, both single-stranded. The method of the invention also provides such msDNAs which contain foreign DNA and RNA fragments in the DNA and RNA portions, respectively, or the RNA-DNA structure. Though different from the known bacterial msDNAs, these molecules are designated as msDNAs or "modified" msDNAs, because they have the characteristics and unique features of msDNAs as described herein.

The invention also provides retrons. Retrons are genetic elements which contain the coding region msr for the msRNA and msd for the msdDNA of the msDNA molecule, respectively, and the gene for reverse transcriptase (RT). The retrons which are new in accordance with the invention, have sequences which are different from known bacterial retrons in that the non-coding region has been shortened, specifically the region between the transcriptional initiation site of the selected promoter and the initiation codon of the RT gene.

The invention also provides retrons which are new by virtue of the fact that, unlike known bacterial retrons, the RT gene is positioned upstream of the msr-msd region, in reverse relationship of that in bacterial retrons. These new retrons produce greater yields of msDNAs.

The invention further provides new types of msDNAs which are new by virtue of having been produced by the novel retrons. These msDNAs contain a foreign DNA fragment in their DNA portion, for instance, a single-stranded fragment complementary to the mRNA of a particular target gene (antisense DNA) and thus, may be valuable tools to inhibit or change the expression of undesirable proteins. Similarly, msDNA can also contain a foreign RNA fragment.

Further novel embodiments of the invention are eucaryotic hosts transfected with retrons which have been isolated from bacterial sources or made synthetically. Also new are eucaryotic hosts transfected with the new vectors discussed above.

Various uses for the new single-stranded RNA-DNA structures are described.

DEPOSIT OF GENETIC MATERIAL

Plasmid YEp521-M1 has been deposited with the American Type Culture Collection (ATCC) under Accession No. 74092.

Plasmid YEp521-M4 has been deposited with the ATCC under Accession No. 74093.

Plasmid YEp521-M5 has been deposited with the ATCC under Accession No. 74094.

BRIEF DESCRIPTION OF THE FIGURES

FIG. 8A shows bands a and b of a sequence polyacrylamide gel for the production of msDNA-Ec67 and FIG. 8B shows a schematic representation of extension of the 3' end of msDNA by AMV-RT and RNase A treatment.

DETAILED DESCRIPTION OF THE FIGURES

Figure 1:
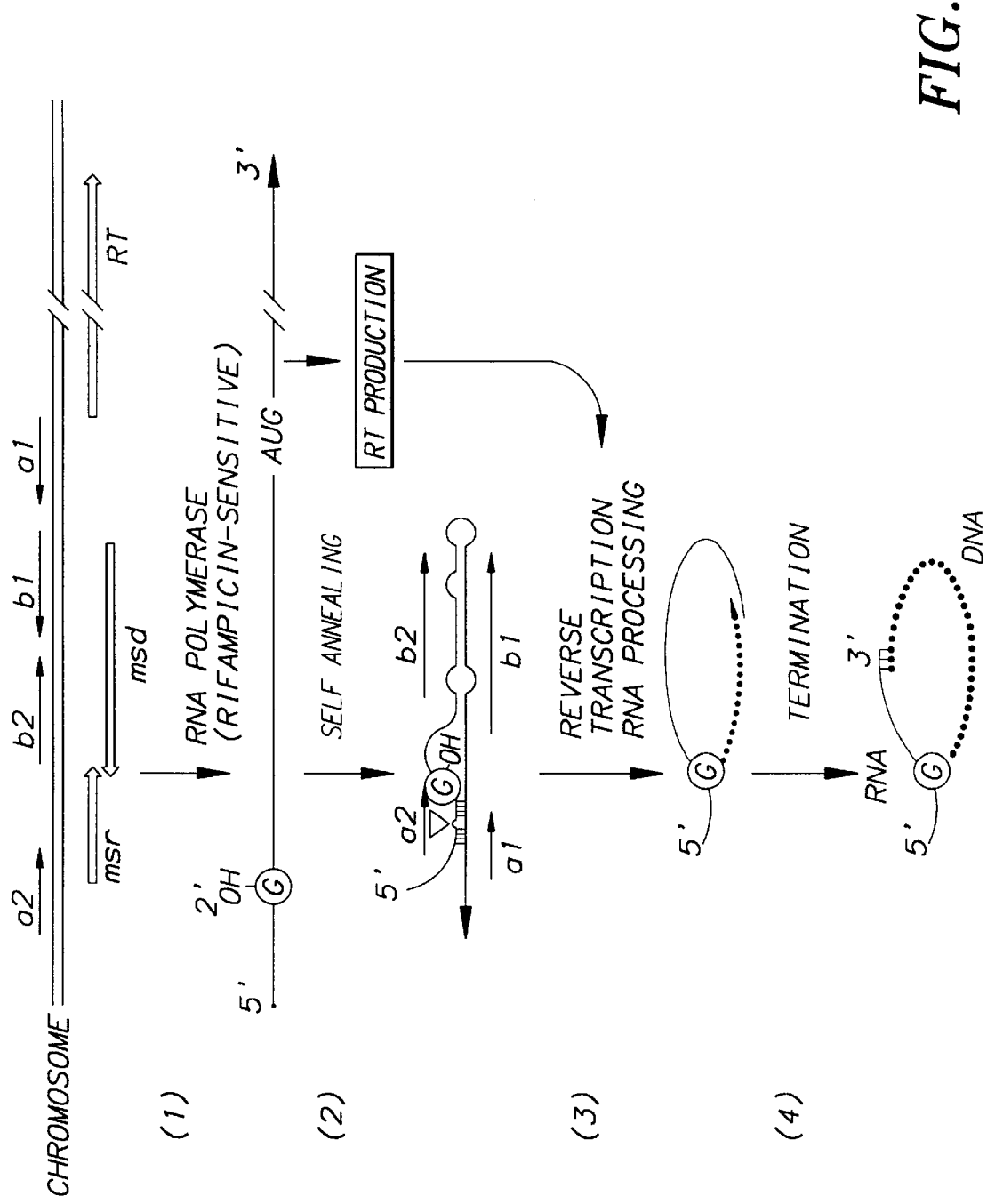
FIG. 1 illustrates the biosynthetic pathway of msDNA synthesis.

FIG. 1 Biosynthetic pathway of msDNA synthesis. The retron region consisting of the msr-msd region and the gene for reverse transcriptase (RT) is shown on the top of the Figure. Solid arrows indicate the locations of two sets of inverted repeats (a1 and a2, and b1 and b2). Open arrows indicate the genes for msdRNA (msr), msDNA (msd), and RT. The primary transcript is considered to encompass the upstream region of msr through the RT gene, which is shown by a thin line at step 1. The thick region in the RNA transcript corresponds to the final msdRNA. The branched G residue is circled, and the initiation codon for RT is also shown. On the folded RNA, a triangle indicates the 5' end processing site at the mismatching base. The dotted lines at steps 3 and 4 represent DNA strands.

Figure 2A:
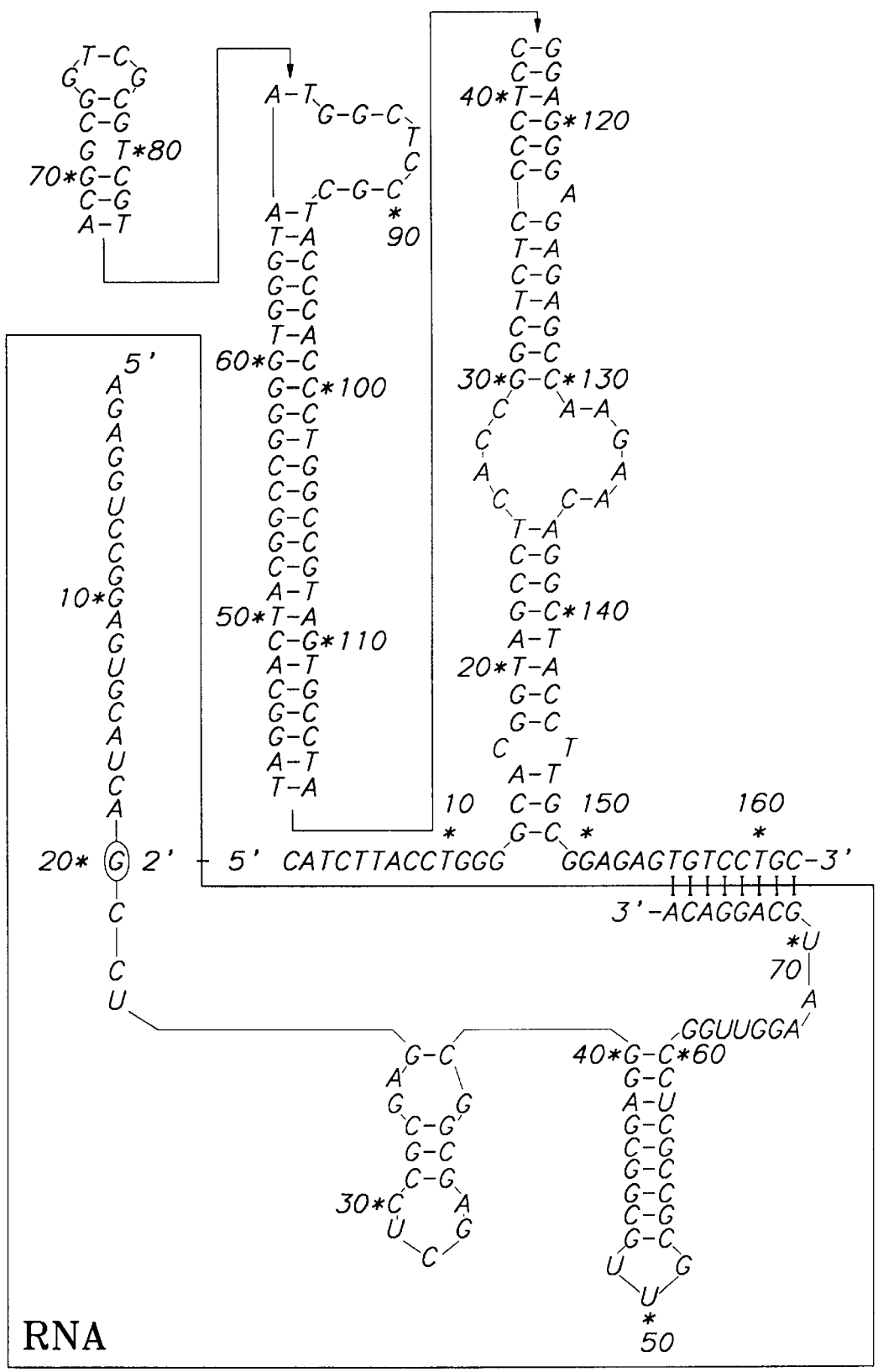
FIG. 2A shows the structure of the typical bacterial msDNAs.
Figure 2B:
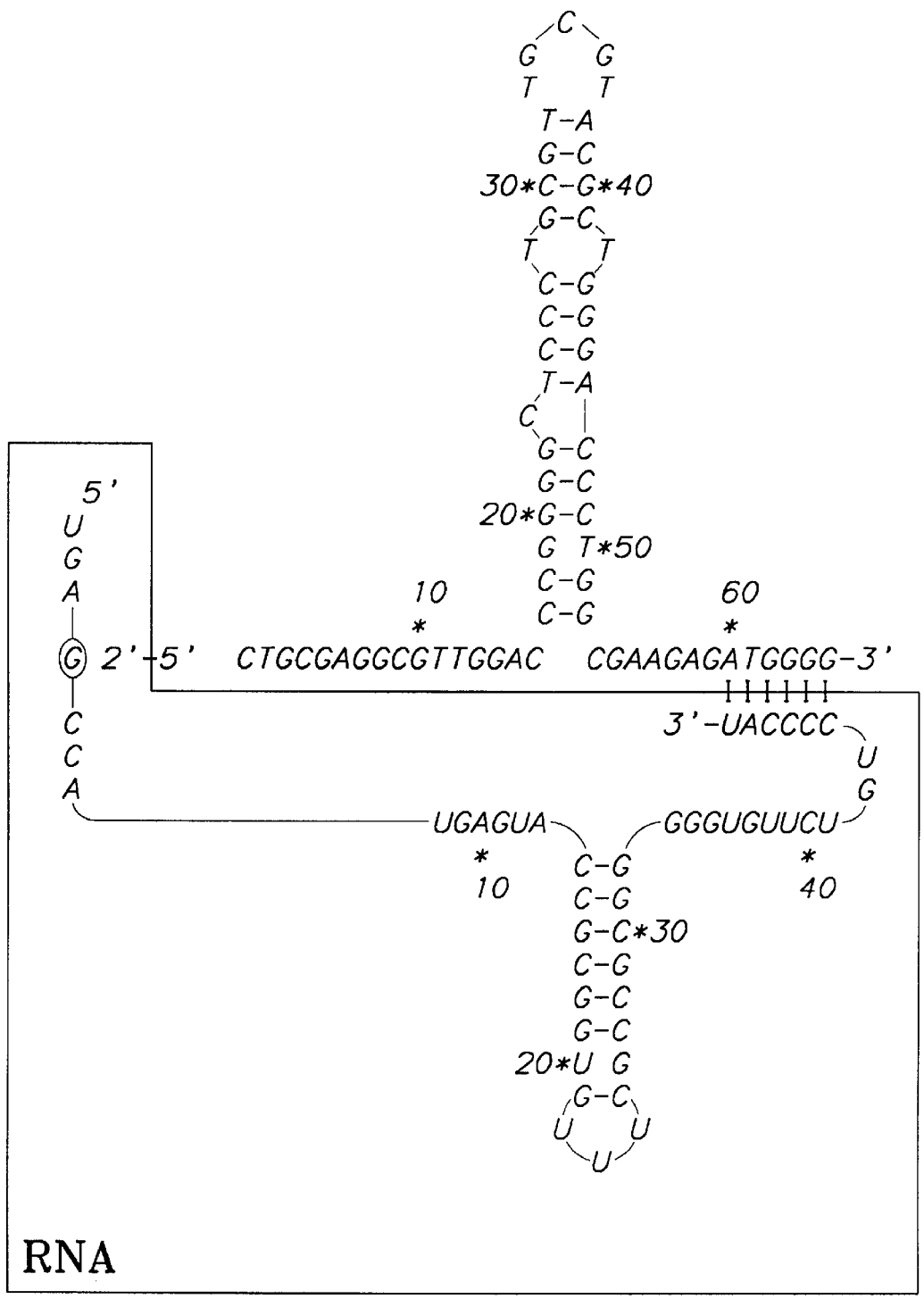
FIG. 2B shows the structure of msDNA-Ye117.
Figure 2C:
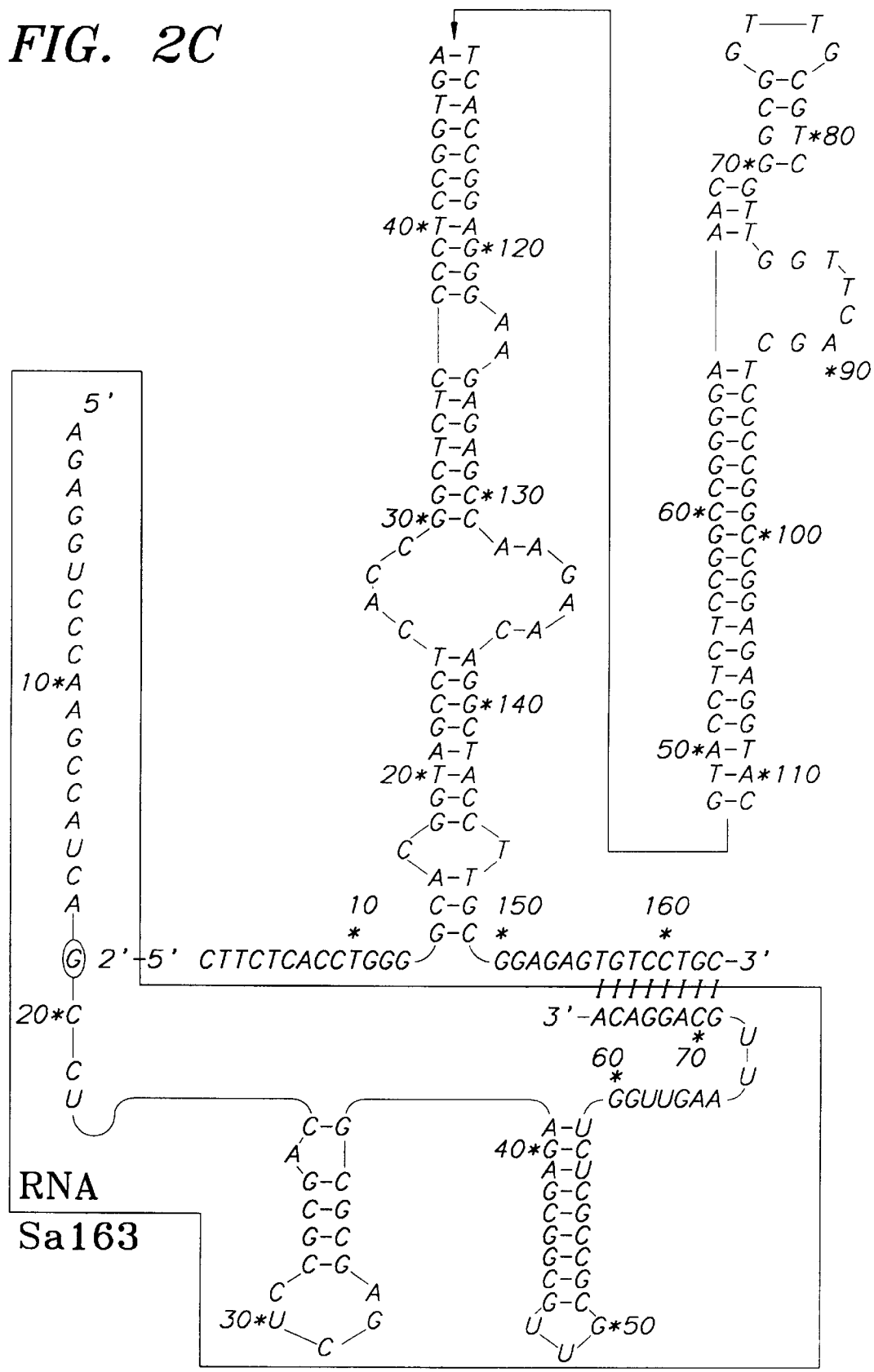
Figure 2D:
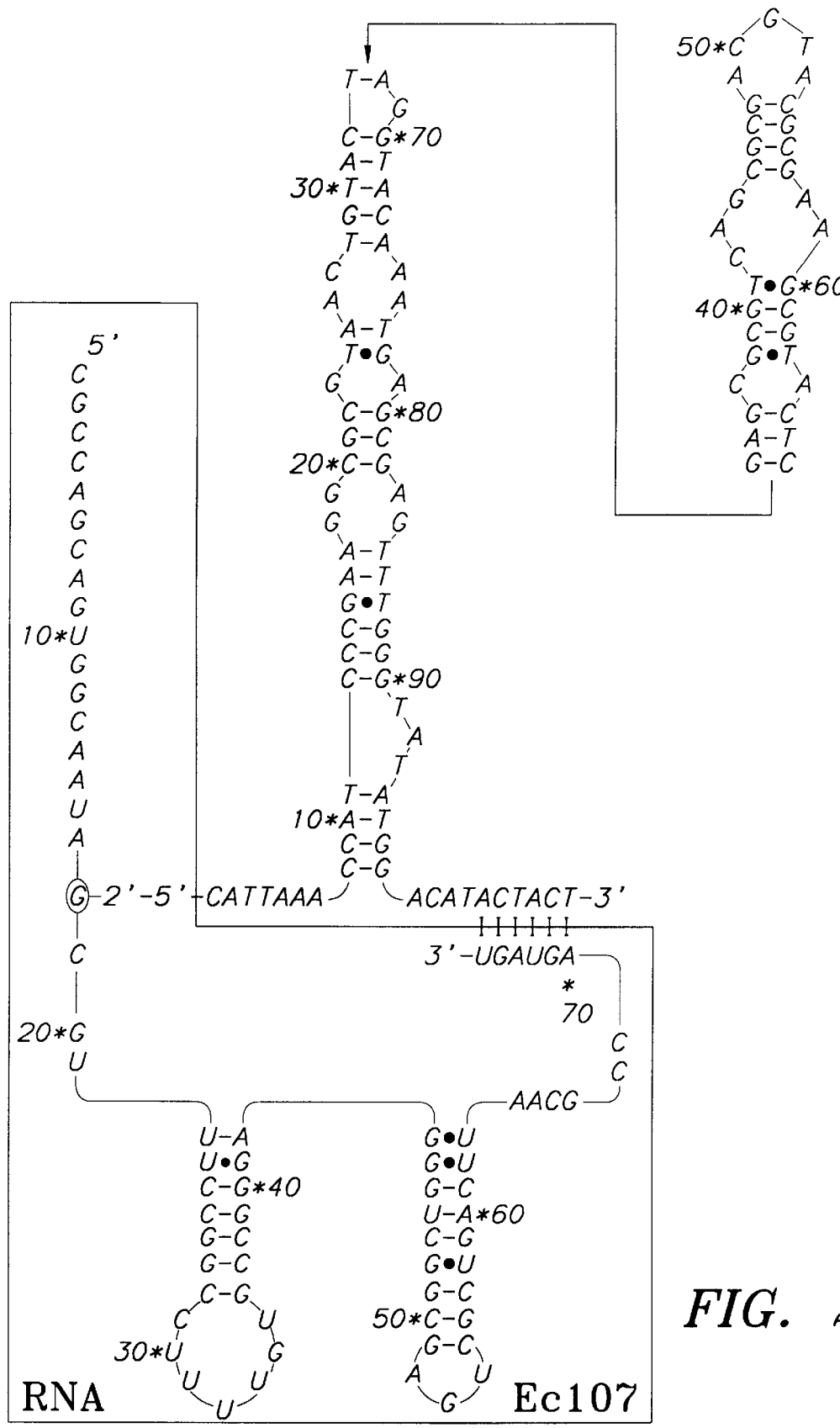
Figure 2E:
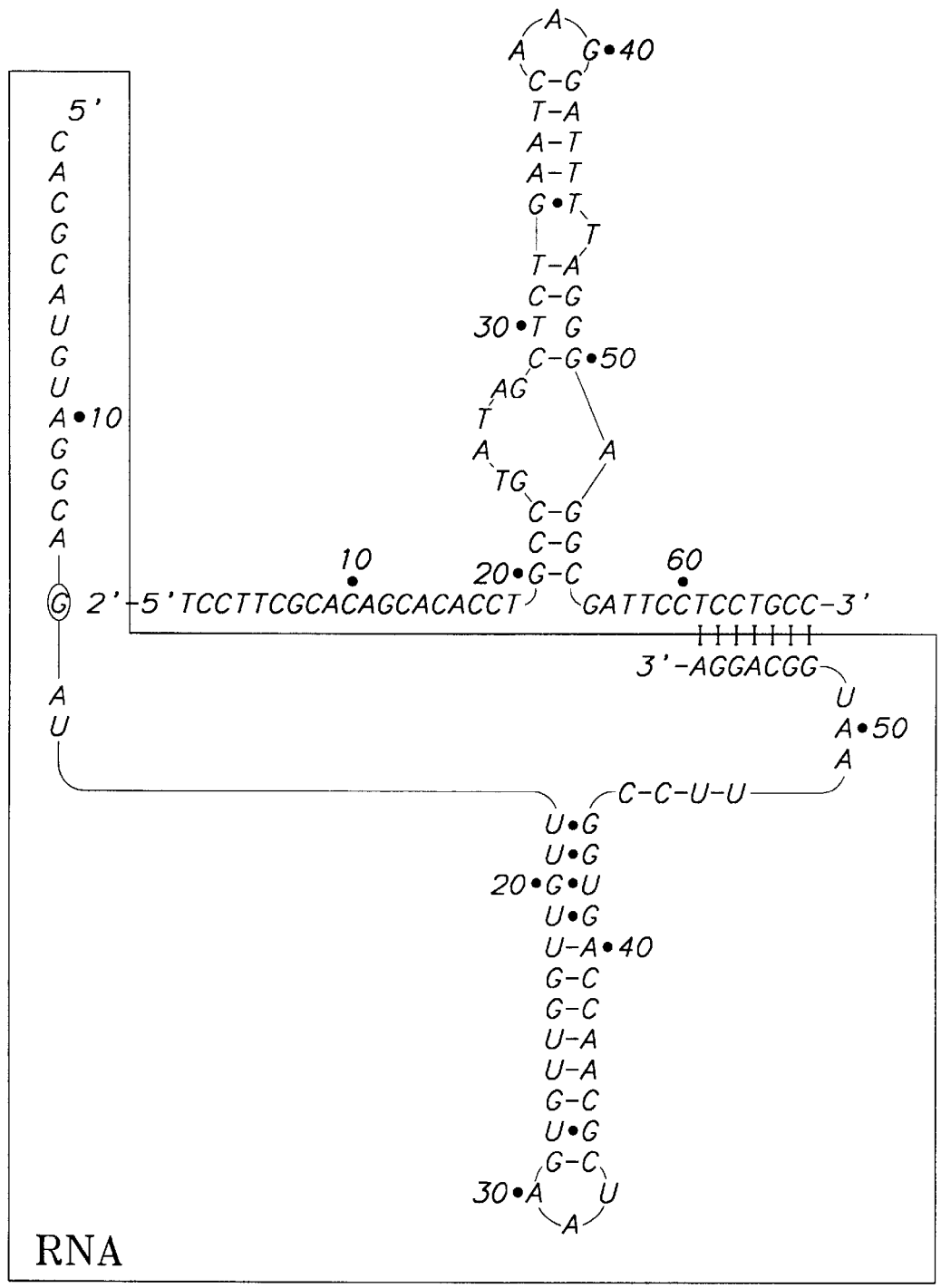
Figure 2F:
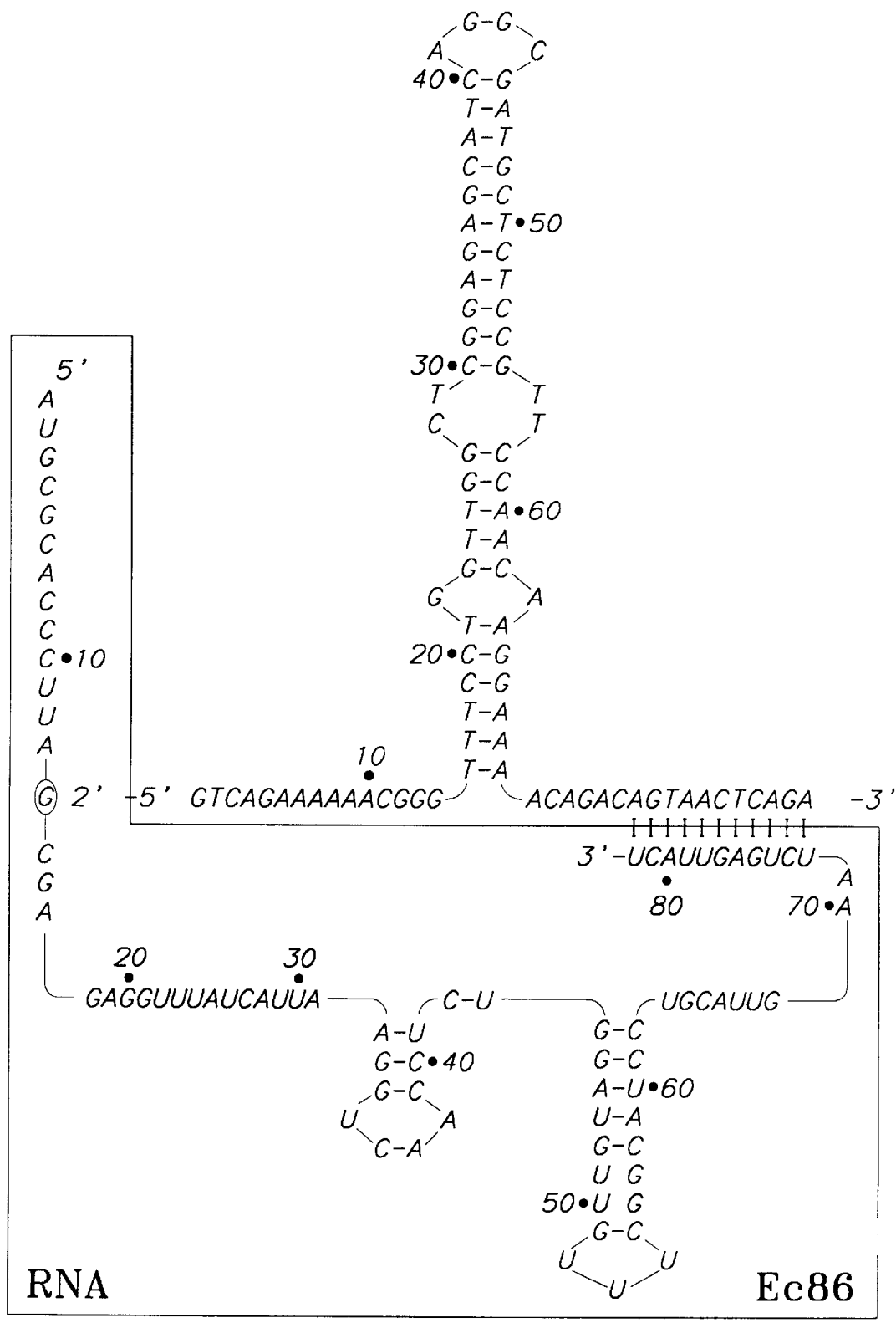
Figure 2G:
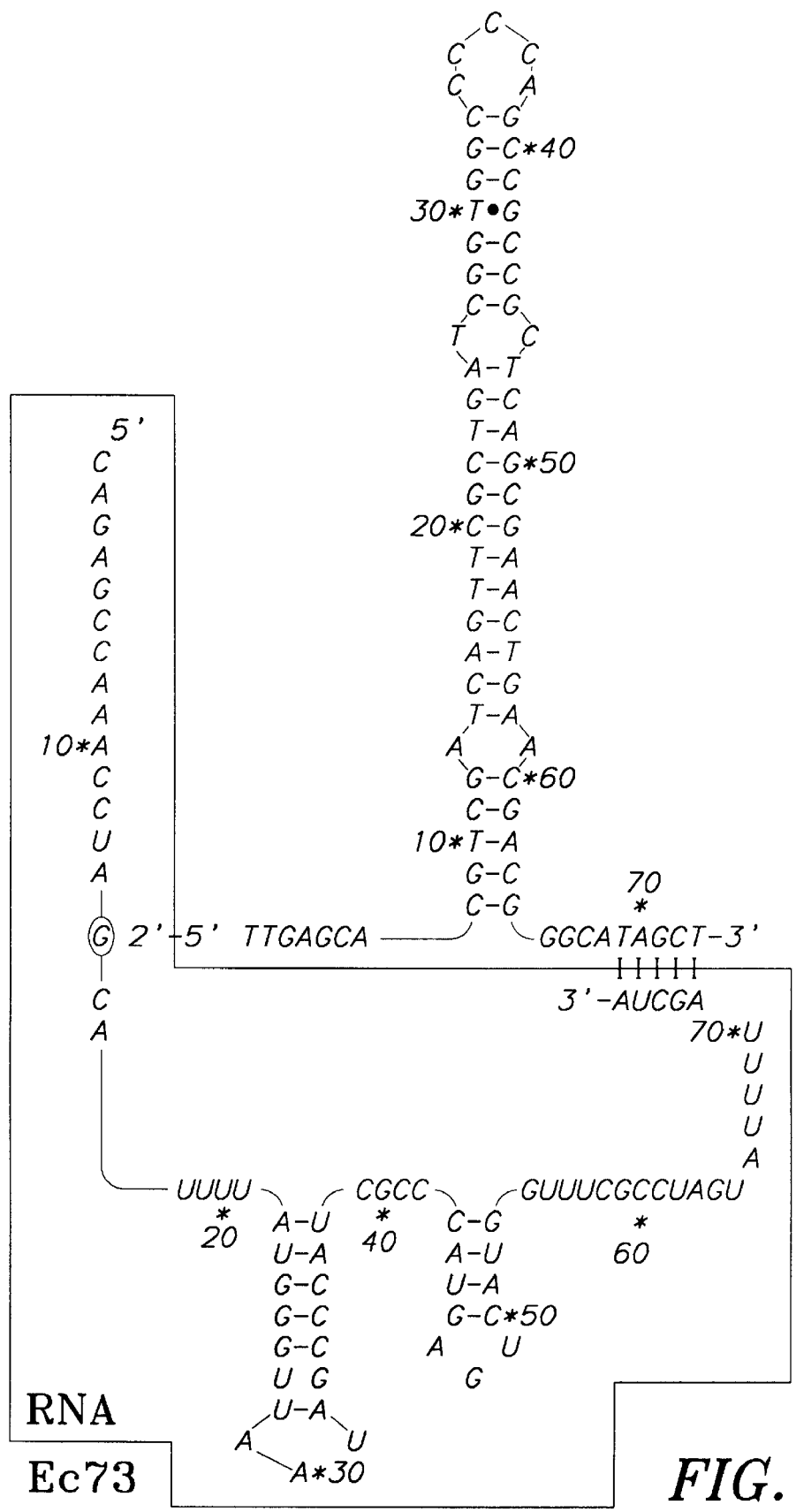
Figure 2H:
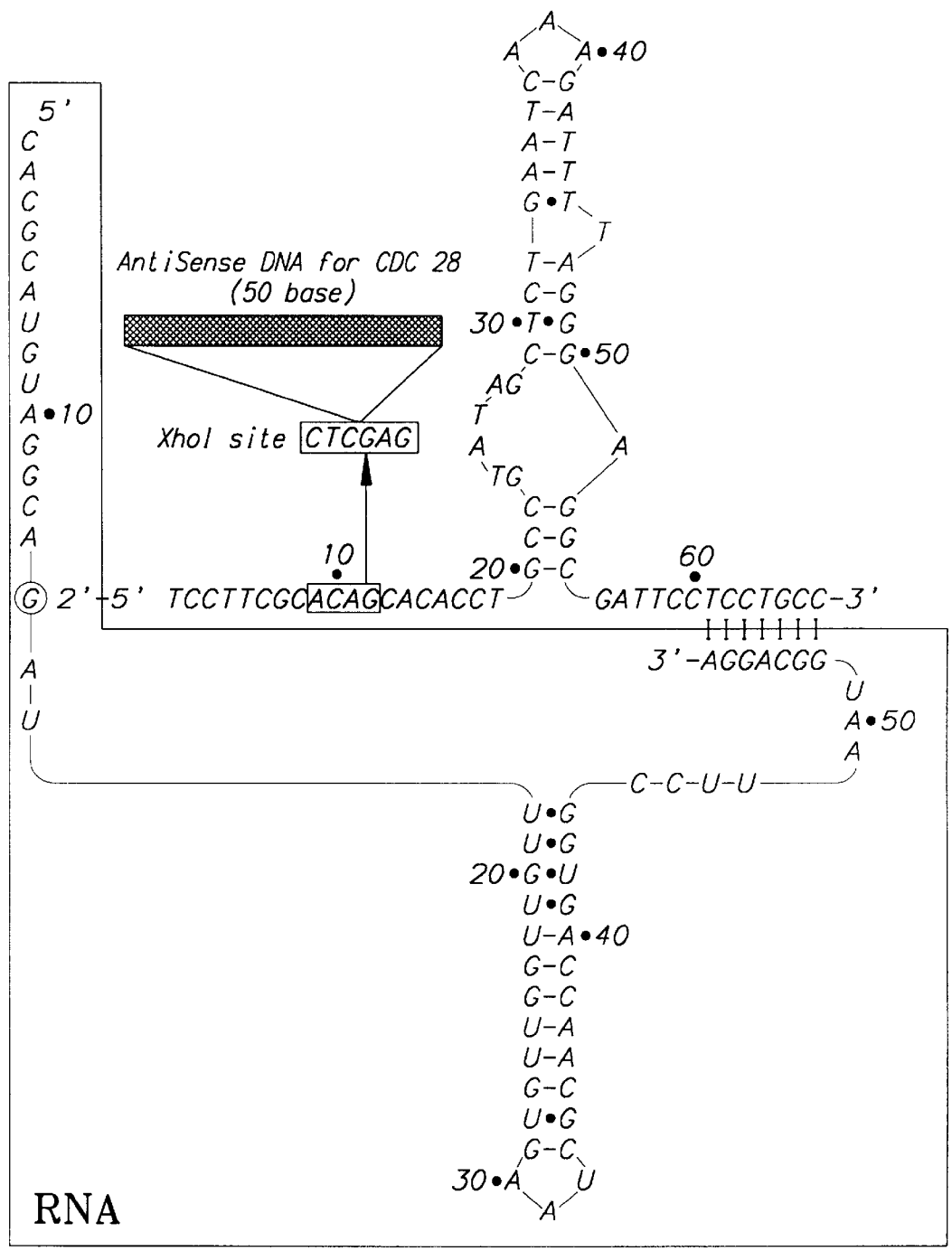

FIGS. 2A and 2B (A) Structures of hybrid DNA-RNA msDNA are shown as follows: Mx162, Mx65, Sa163, Ec107, Ec67, Ec86 and Ec73. (Ann. Rev. Microbiol., 45, 163–186 (1991)) (B) Structure of hybrid DNA-RNA msDNA-Ye117 is shown.

Figure 3:
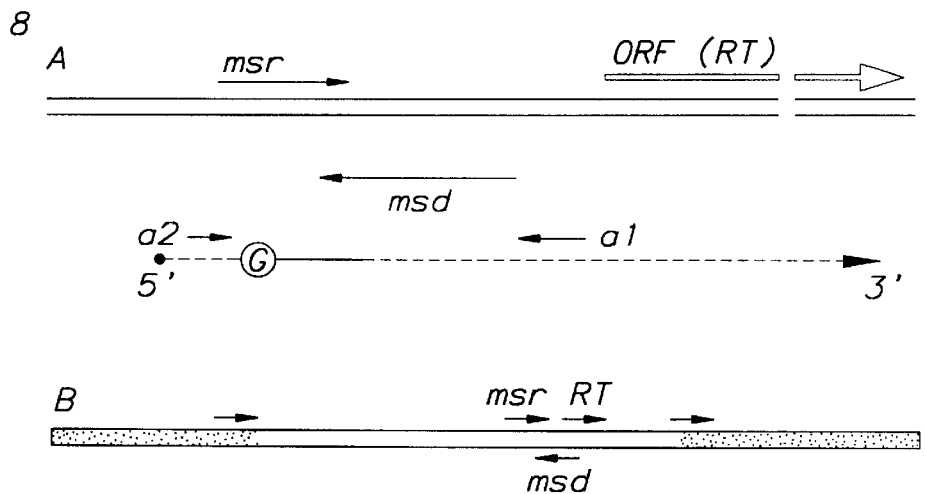
FIG. 3 shows the arrangement of genes in the retroelement responsible for the production of msDNAs.

FIG. 3 Arrangement of genes in the retron element responsible for the production of msDNA. A single-copy retroelement on the bacterial chromosome contains the region required for the production of msDNA. All known msDNA coding regions contain three genes organized in a similar manner, as shown in (A): A gene, msd, codes for the DNA strand of msDNA. A second gene (msr) is situated, 5' to 3', in the opposite direction and codes for the RNA strand of msDNA. A closely positioned ORF codes for the RT. Transcription of this region initiates at or near the 5' end of msr and extends beyond msd to include the ORF. A set of inverted repeat sequences, a1 and a2, is also conserved among msDNA coding regions (short arrows). The circled G corresponds to the residue in the RNA that will contain the 2',5' branch linkage in msDNA (see also FIG. 8A). (B) For the E coli retron Ec67, the region encoding msDNA is only a small part of a large element found on the chromosome (open bar). The junction of the Ec67 retron with the host chromosome is flanked by 26-base directly repeated chromosomal sequences, as shown by arrows. The Figure is not drawn to scale.

Figure 4:
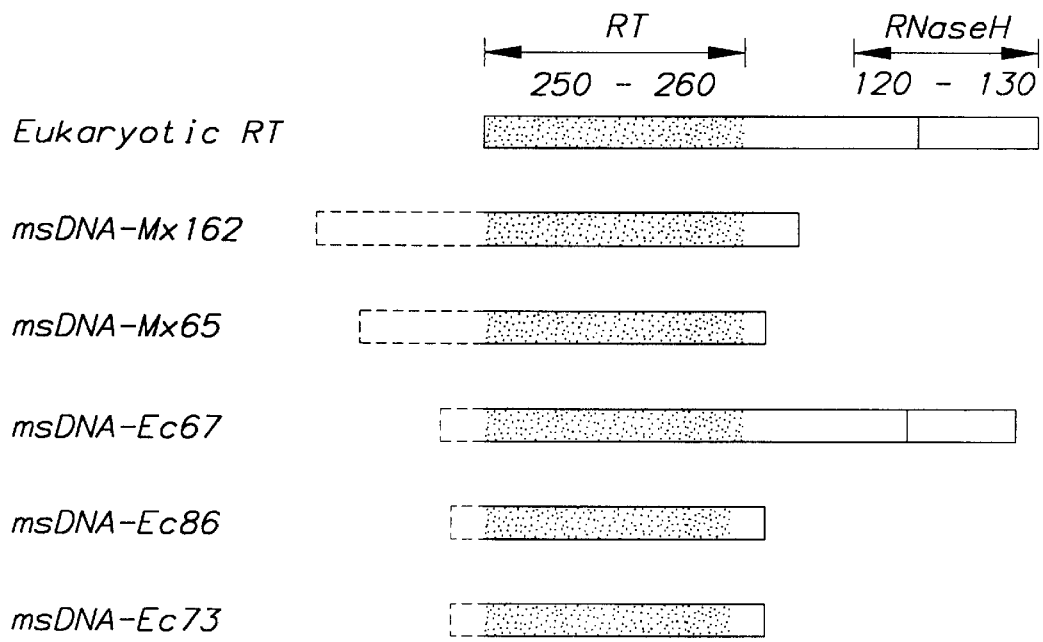
FIG. 4 shows a comparison of the domain structures of various bacterial RTs.

FIG. 4 Domain structures of various bacterial RTs. The regions with closed bars and with stippled bars represent the RT and RNase H domains, respectively.

FIG. 4 Yeast expression vectors YEp51 (7.3-kb) and YEp52 (6.6-kb). The structures of two yeast expression vectors are diagrammed. Both are composed of sequences from the yeast plasmid 2-$\mu$m circle (smooth single line) spanning REP3 (◯) and the origin of replication (◯), from the bacterial plasmid pBR322 (jagged single line) spanning the ColE1 origin of replication and the gene conferring ampicillin resistance, from the yeast genome spanning the gene LEU2 (◯), and from the region 5' to the yeast GAL10 gene (◯), extending from the Sau3A site at −495 from the transcription-initiation site to the SalI site present in plasmid pNN78-Δ4 at +13. A cloned gene inserted in YEp51 in the SalI, SalI-to-BamHI, SalI-to-HindIII, or SalI-to-BclI sites pointed labelled I in the Figure, terminating at a site in the 2-$\mu$m-circle sequences indicated by the blocked arrow (T). Similar transcription would be obtained with genes inserted in the HindIII or HindIII or BclI sites of YEp52. Restriction enzymes: R, EcoR1; H, HindIII; B, BamHI; S, SalI; P, PstI; Bc, BclI. See Broach et al., *Experimental Manipulation of Gene Expression*, Academic Press Inc., New York, 1983.

Figure 6:
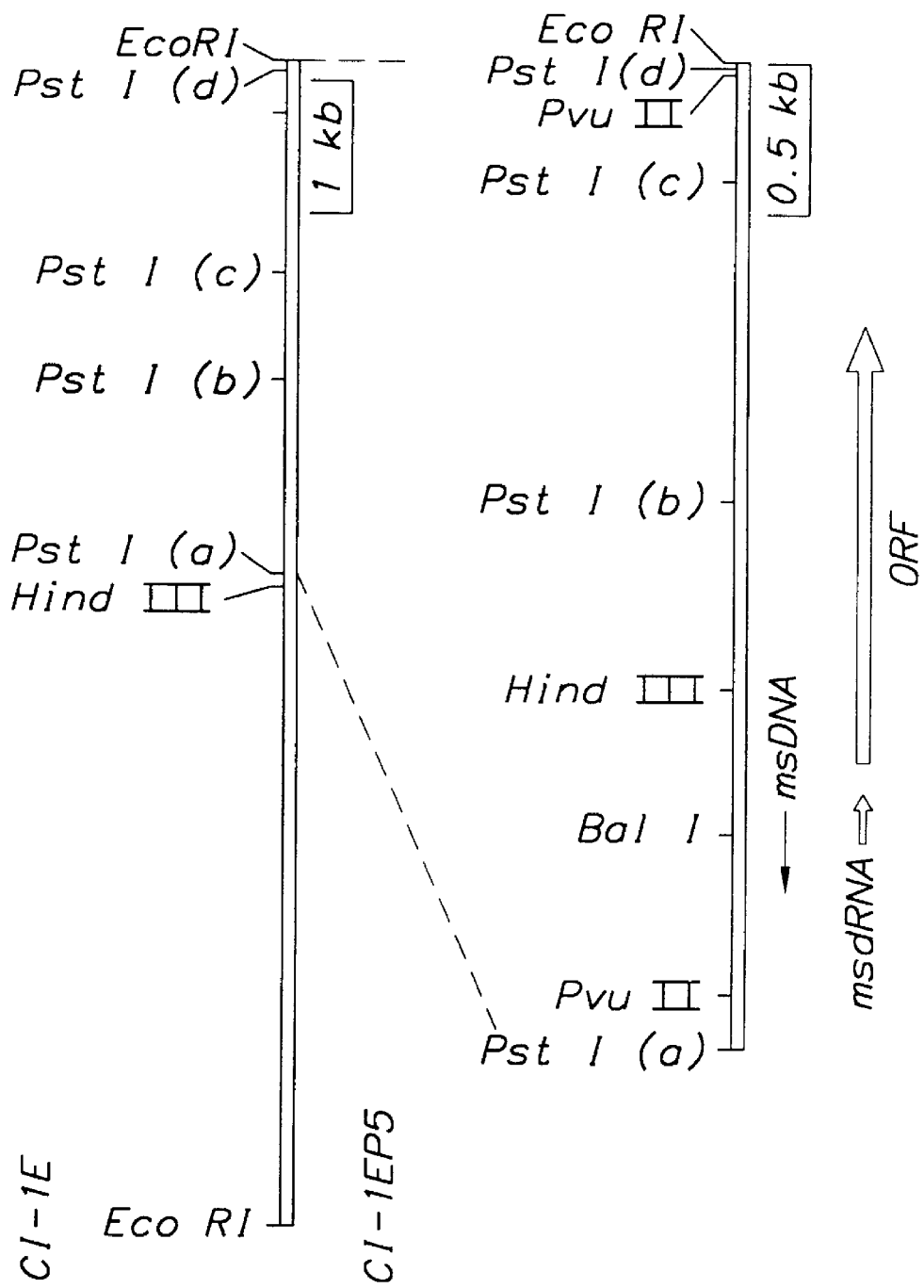
FIG. 6 shows the restriction map of the 11.6-kb EcoR1 fragment.

FIG. 6 Restriction map of the 11.6-kb EcoRI fragment. In the Cl-1E map, the left-hand half (EcoRI to HindIII) was not mapped. In the Cl1EP5 map, the locations and the orientations of msDNA and msdRNA are indicated by a small arrow and an open arrow, respectively. A large solid arrow represents an ORF and its orientation. See Lampson et al., *Science*, 243, 1033–1038 (1989).

Figure 7:
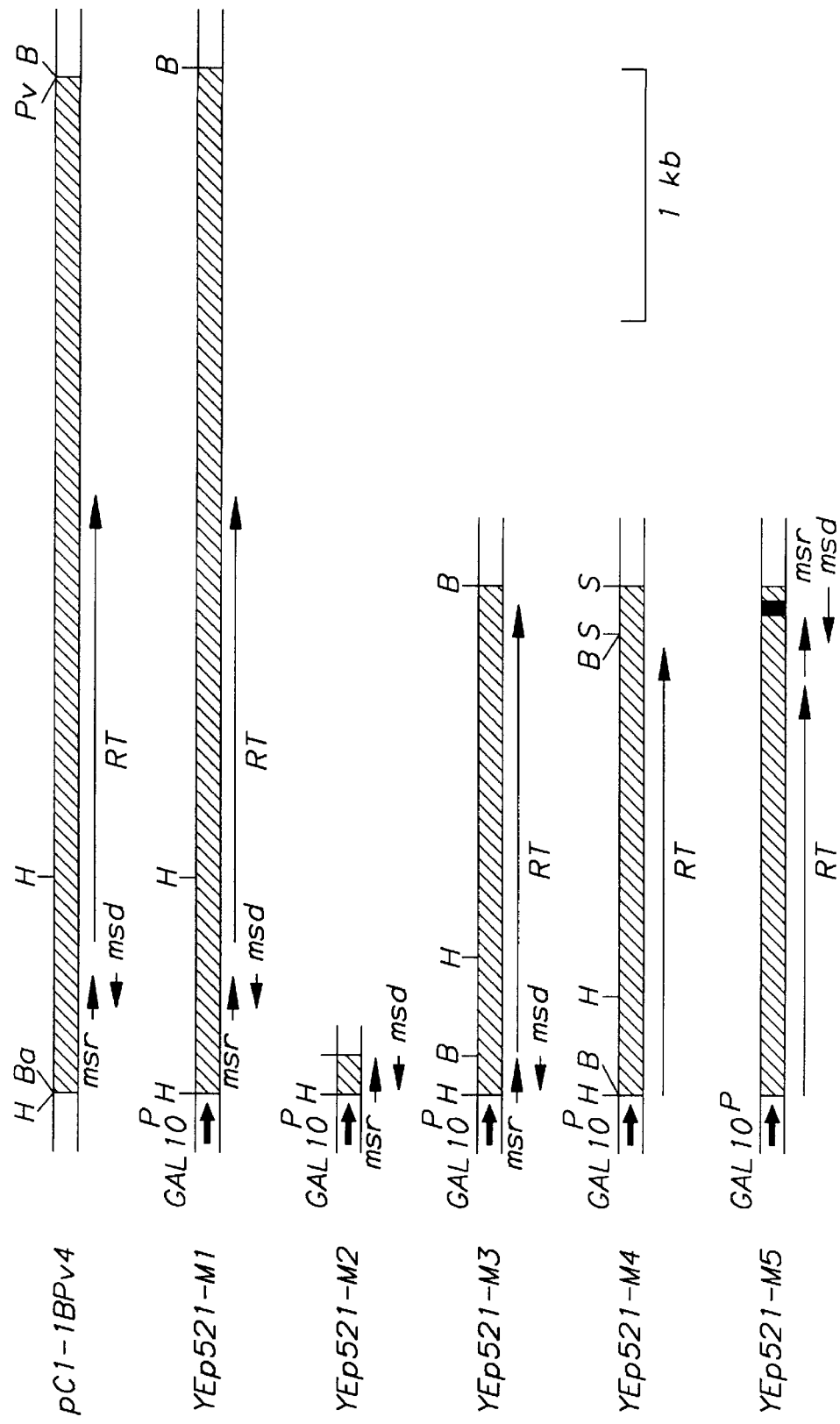
FIG. 7 shows a diagrammatic representation of plasmid PC1-1BPv4, YEp521-M1, YEp521-M2, YEp521-M3, YEp521-M4 and YEP521-M5.

FIG. 7 Diagrammatic representation of plasmid PC1-1BPv4, YEp521-M1, -M2, -M3, -M4 and M-5. Diagrams show only the regions (shaded bars) inserted in the yeast vector, YEp521. These regions contain retron-Ec67 and restriction sites shown area only those which are used for the construction of plasmids. Short arrows with msr or msd are the locations and the orientations of msdRNA and msDNA. Long arrows with RT represent the gene for RT and its orientation. Thick arrows represent the GAL10 promoter and its orientation of transcription. Letters on top of bars are the sites of restriction enzymes: H, HindIII; Ba, BalI; Pv, PvuII; B, BamHI; and S, SmaI.

Figure 8A:
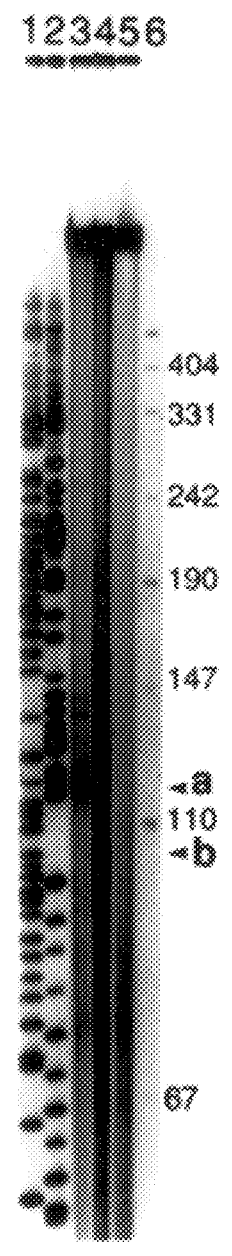
Figure 8B:
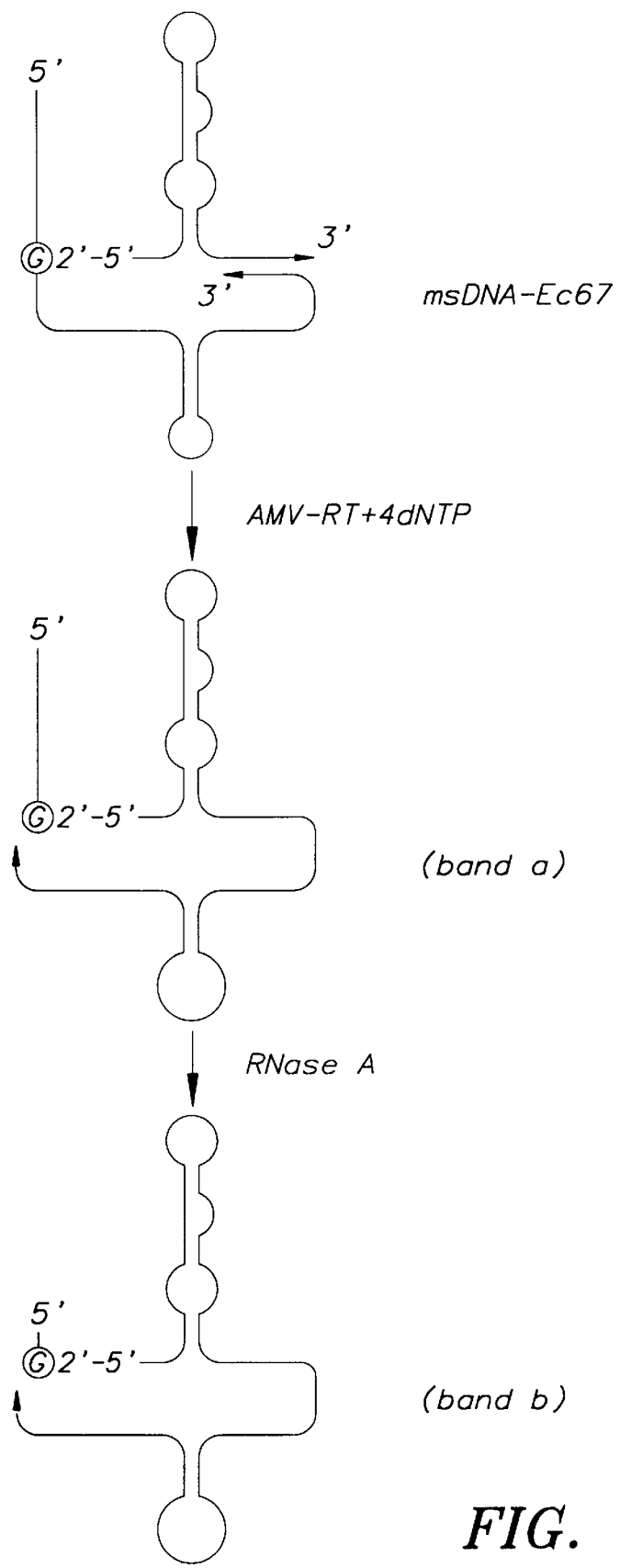

FIGS. 8A and 8B A sequence polyacrylamide gel of the production of msDNA-Ec67 in *S. cerevisiae*.

(A) Total RNA prepared from 0.9 ml of a late-log culture was used for detecting msDNA with AMV-RT as described herein below. The RT reaction mixture was subjected to electrophoresis on a 6% sequence-urea-gel. An aliquot of the reaction mixture was treated with RNase A prior to gel electrophoresis. Lanes 1 and 2 (G and C lanes, respectively) are DNA sequence ladders of pUC19 sequenced by chain termination method (Sanger et al., *Proc. Natl. Acad. Sci. USA*, 74, 5463–5467 (1977)) for size marks; lane 3, the AMV-RT products with total RNA from yeast cells harboring YEp521-M1; lane 4, the same sample as lane 3 except that it was treated with RNase A prior to gel electrophoresis; lane 5, the AMV-RT products with total RNA from yeast cell harboring YEp521. The sample was treated with RNase A.

Lane 6 is an MspI digest of pBR322 labeled with [γ-$^{32}$P] dCTP with the Klenow fragment of DNA polymerase I. Numbers at the right-hand side indicate fragment sizes in base pairs and arrows with letters indicate positions of msDNA.

(B) Schematic representation of extension of the 3' end of msDNA-Ec67 by AMV-RT and RNase A treatment.

Figure 9A:
FIG. 9 shows Southern blot hybridization of msDNA-Ec67 produced in S. cerevisiae.
Figure 9B:
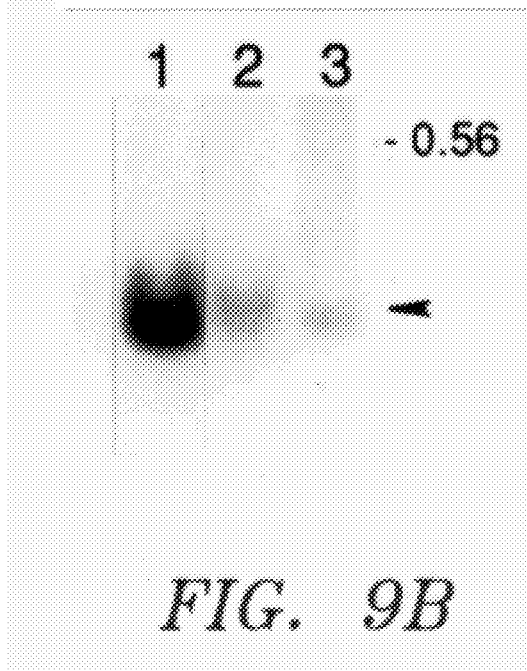

FIG. 9 Southern blot hybridization of msDNA-Ec67 produced in S. cerevisiae.

(A) Total RNA fractions prepared from a 2.5 ml culture of yeast cells harboring YEp521-M1 (lane 1), and YEp521-M2 (lane 2) and from E. coli CL83 harboring pCL-1EP5c (lane 3) were used. After blotted to the nylon membrane filter, msDNA-Ec67 was detected with the nick-translated 140-bp msr-msd DNA fragment as a probe. An arrowhead indicates the position of msDNA-Ec67.

(B) Production of msdDNA-Ec67 in S. cerevisiae harboring YEp521-M1, -M3, and -M4. Total RNA fractions prepared from a 2.5 ml culture of yeast cells harboring YEp521-M1 (lane 3), -M3 (lane 2), and -M4 (lane 1) were used for Southern blot hybridization as described in (A). An arrowhead indicates the position of msDNA-Ec67.

Figure 10:
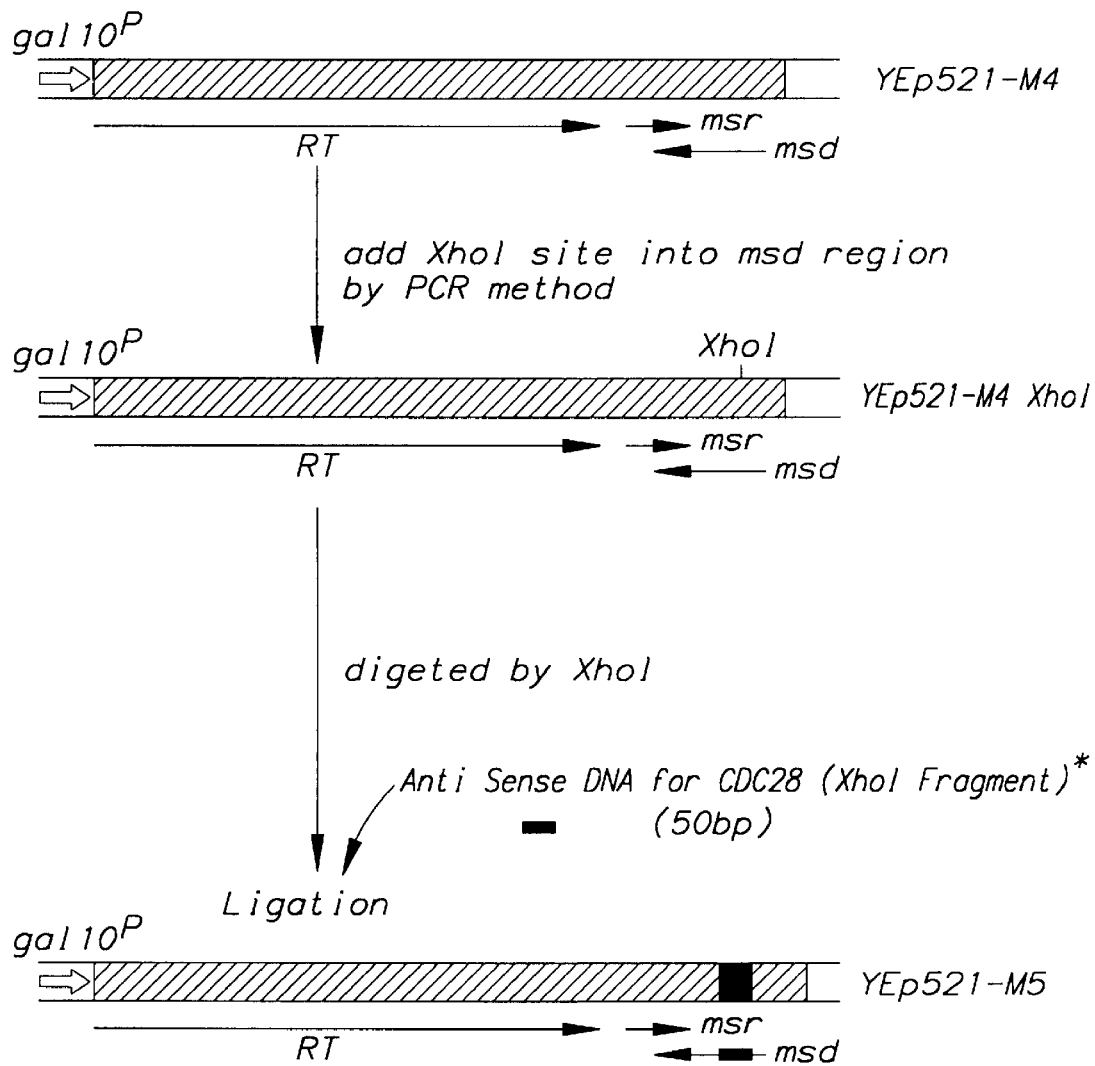
FIG. 10 shows a diagrammatic representation of plasmid YEp521-M5. Darkened region in the retron represents 50-bp antisense DNA for cdc28 (cloned into the XhoI site) inserted into the msd region of retron Ec67. Also shown in the 50-bp antisense DNA for cdc28.

FIG. 10 YEp521-M5 was constructed from YEp521-M4 by inserting into the msd region an XhoI site and into that site, cloning a 50-bp extraneous (foreign) dsDNA fragment which is complementary to mRNA of cdc28. The XhoI site was added into the msd region of YEp521-M4 by PCR. This construct was then digested by XhoI; then the antisense DNA was ligated into the msd region of retron Ec67. This plasmid was transfected into yeast (SP-1) and the subsequently expressed msDNA designated herein as msDNA-Ye117. This is a novel structure.

DETAILED DESCRIPTION OF ILLUSTRATIVE EMBODIMENTS OF THE INVENTION

In accordance with this invention, it has been discovered that a transfected yeast, *Saccharomyces cerevisiae*, produces a genetic structure, described as a synthesized, branched RNA-linked multicopy single-stranded DNA (msDNA). One such msDNA produced was msDNA-Ec67. msDNA-Ec67 was synthesized from retron-Ec67.

The production of other representative msDNAs is described.

Several msDNAs have been described in the literature. Some of these are the following: Mx162 (Dhundale et al., Cell, 51, 1105–1112, 1987); Mx65 (Dhundale et al., J. Biol. Chem., 263, 9055–9058, 1988b); Sa163 (Furuichi et al., Cell, 48, 47–52, 1987a and Furuichi et al., Cell, 48, 55–62, 1987b); Ec67 (Lampson et al., Science, 243, 1033–1038, 1989b); Ec86 (Lim and Maas, Cell, 56, 891–904, 1989); Ec73 (Sun et al., J. Bacteriol., 173, 4171–4181, 1991); Ec107 (Herzer et al., Mol. Microbiol., submitted, August 1991); msDNA from E. coliB (Lim and Maas, Cell, 56, 891–904, 1989).

The msDNAs are often referred to in the literature by a numeral preceded by a suffix indicating a host origin. For instance, "Mx" referring to *Myxococcus xanthus,* and "Ec", referring to *E. coli* and "Sa" to *Stigmatella aurantiaca.* msDNAs are unique molecules which in spite of extensive diversity, share similar structural features. Generically, msDNA may be described as being a molecule which comprises a branched RNA which is covalently linked to a single-stranded DNA by a 2',5'-phosphodiester bond between the 2'-OH group of an internal rG residue and the 5'-phosphate of the DNA molecule, and which RNA is non-covalently linked to the DNA by base pairing between the complementary 3' ends of the RNA and DNA molecules, which RNA and DNA form the stable stem-loop secondary structures. The msDNA molecule is encoded by a primary RNA transcript, pre-msDNA, which contains an open-reading frame (ORF) downstream of the msr locus encoding a polypeptide which has sequence similarity with retroviral RTs and a highly conserved sequence common to RTs.

The pre-msDNA may alternatively contain its ORF upstream of the msr locus, in which event the retron will be of like construction.

In FIG. 2 which shows typical msDNAs, the RNA portion of the molecule is shown "boxed"; the balance of the structure being the ssDNA portion.

It will be noted that the molecules all show a branched rG residue, a DNA-RNA hybrid at the 3' ends of the msDNA and msdRNA, and a stem-loop structure in the RNA and DNA strands. The branching ribonucleotide, G, is circled and the 2',5'-phosphodiester linkage to the first deoxynucleotide is indicated.

A retron is a small genetic element to date found to be of 1.3 to 2.5-kb in length constituted of an msr-msd region and by the gene for encoding reverse transcriptase (RT). The gene coding for the single stranded DNA portion of the msDNA is indicated by "msd"; the gene coding for the RNA portion of the hybrid molecule msDNA is indicated by "msr".

A comparison of all known msDNA coding regions reveal that this locus contains three genes organized in a similar manner. See FIG. 3. A gene called msd codes for the DNA portion of msDNA. A second gene, msr, is situated 5' to 3', in the opposite orientation of msd, and codes for the RNA chain. Thus the genes msd and msr are covergently oriented so that their respective 3' ends overlap by several bases.

This overlap is equivalent to the H-bonded DNA-RNA structure formed by the overlapping 3' ends of the RNA and DNA strands in the msDNA molecule. For Mx162, the overlapping msd-msr genes, like the hybrid structure of the msDNA they produce, comprise 8 base pairs. See Table I for typical overlap lengths of various msDNAs.

Determination of the nucleotide sequence in the vicinity of the msd-msr genes revealed a closely-linked open reading frame (ORF). This ORF is located immediately upstream from msd, but is transcribed in the same direction as msr (as shown in FIG. 7). The initiation codon of the ORF is situated as close as 19 base-pairs from the start of the msd gene for the Ec86 retron of *E. coli* B, bus as much as 77 base pairs for the Mx162 retron of *M. xanthus.*

Another conserved feature of the chromosomal locus that codes for msDNA is a set of inverted repeat sequences, designated A1 and a2. Sequence a1 is located just upstream from the start of the msd gene, while sequence a2 is positioned immediately 5' to the G residue in the msr gene that forms the 2',5' branch linkage in the msDNA molecule (FIG. 4). The inverted repeats display a large degree of nucleotide sequence diversity among the different known loci encoding msDNA, as well as differences in size. For example, the inverted repeats (a1 and a2) found in the retron locus encoding Mx162 are 34 nucleotides long, while the inverted repeats for the Ec86 retron of *E. coli* B are only 12 bases in size. Despite their diversity, these repeat sequences are located in the same positions (as shown in FIG. 3) for all known loci encoding msDNA. As discussed in more detail below, the position of these inverted repeat sequences is critical to the synthesis of msDNA.

It will be helpful to refer to the above discussion when the aspects of the invention are discussed which provide for an inversion in the organization (position inversion) of the RT gene with respect to the msr-msd coding region, and in the discussion of shortening the non-coding region between the transcriptional initiation site and the initiation codon AUG of the RT gene.

The promoter for the msr-msd region is upstream of msr. Transcription is from left to right, encompassing the entire region including the RT gene. As described in further detail hereinafter, the replicating vehicle for transfecting the eucaryote host may harbor one promoter for the msr-msd and the RT, or it may contain two promoters, one for the msr-msd region and the other for the RT.

It is within the scope of the invention that retrons be constructed to yield an msDNA which differs from the typical msDNAs by features other than the common, conserved and characteristic features of msDNAs described above. For instance, it is not excluded that the length and/or location of the set of IRs a1 and a2 in the retrons be varied providing they remain in the same location discussed above. Thus, the size and/or location of the loops in the stems of the msDNA can be varied. The secondary structure (the stems) may contain one or more loops. The loops typically contain 4 to 30 bases, such as 10 to 30 bases or 10 to 20 bases. The loops may contain more than 30 bases, such as 30 to 50 or 30 to 100 bases.

Further, it is not excluded that the extent of or overlap of the base pairing of the 3' ends of DNA and RNA in the msDNAs be influenced (increased or decreased) by appropriate manipulations. Whether such variations will be desirable will depend on the ultimate utility proposed for these msDNAs.

General Features of msDNAs. Table I is a summary of the structure of representative retrons.

Reverse Transcriptase (RT). The domain structures of bacterial RTs of representative retrons are shown in FIG. 4.

The RT gene is normally located downstream from the msr-msd region. In the new retrons which differ from the bacterial retrons, their relative positions are reversed, the msr-msd region is located downstream of the RT gene.

The biosynthesis of msDNAs has been described in Inouye & Inouye, Ann. Rev. Microbiol., 45, 163–186 (1991b) and Herzer et al., Mol. Microbiol., submitted, August 1991. A schematic of the synthesis is shown in FIG. 1. A primary transcript (pre-msdRNA) is considered to encompass the upstream region of msr through the RT gene, which is by reference to FIG. 1, shown by a thin line at step 1. The thick region in the RNA transcript corresponds to the final msdRNA. The branched G residue is circled, and the initiation codon for RT is also shown. On the folded RNA, a triangle indicates the 5' end processing site at the mismatching base. The dotted lines at steps 3 and 4 represent DNA strands.

The primary transcript from the msr-msd region is believed to serve not only as a template but also as a primer to produce the msDNA. Synthesis of msDNA is primed from an internal rG residue of the RNA transcript using its 2'-OH group. Thus, msDNA is branched out from this rG residue by a 2'-5'-phosphodiester linkage.

There will be described hereinafter the transfection of a typical eucaryotic cell, yeast cells harboring plasmids which contain a retron (which includes the RT gene) for expression of the desired msDNAs. Preferably, RT gene used to express the msDNA is from the same source as that for the genes for the DNA and RNA portions of the msDNA to be expressed. Any RT capable of promoting the production of msDNA from a template may be used. The following reverse transcriptases are examples of RTs which may be used, Sa163-RT, Mx162-RT, Mx65-RT, Ec67-RT, Ec86-RT, Ec73-RT, Ec107-RT, and bacterial reverse transcriptases from bacteria such as Proteus, Klebsiella, Salmonella, Rhizobium, Bradyrhizobium, and Nannocystis, or viral reverse transcriptases from viruses, such as retroviruses. The following description is of a best mode to date to express msDNA-Ec67 from its retron, Ec67.

1. Synthesis of msDNA-Ec67. For the expression of msDNA-Ec67, plasmid YEp52 was used. Plasmid YEp521 was constructed by introducing the multiple cloning sites of pUC19 (Yanisch-Perron et al., Gene, 33, 103–119, 1985) into YEp52, which was designed to obtain high-level, inducible expression of a cloned gene under the GAL10 promoter in yeast. YEp52 contains the ColE1 origin of replication (OR), a promoter of the GAL10 gene, LEU2, the $2\mu$-circle origin of replication, and the $2$-$\mu$ circle REP3 locus. See FIG. 5. See Broach et al., Experimental Manipulation of Gene Expression, Academic Press Inc., New York, 1983.

Figure 5A:
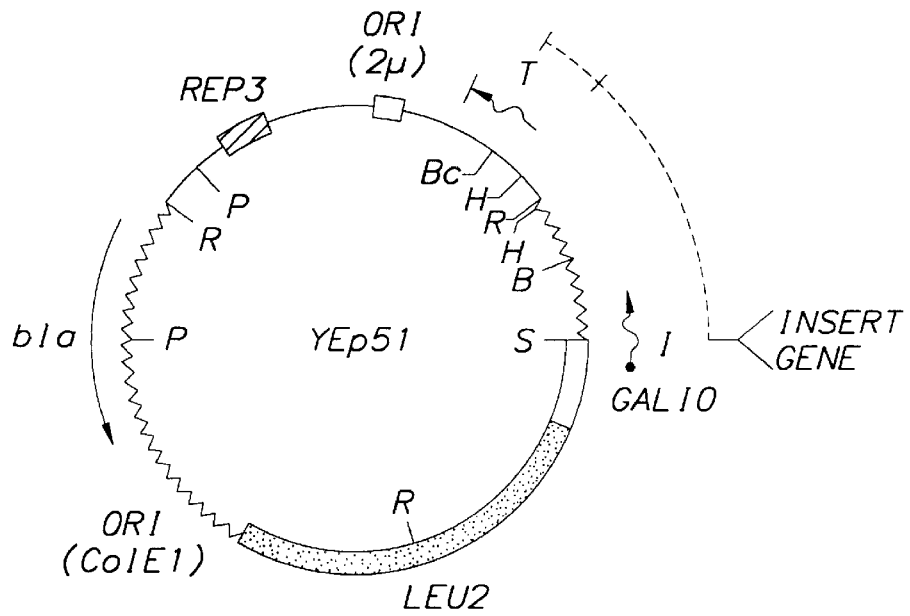
FIG. 5 shows plasmids YEp51 and YEp52.
Figure 5B:
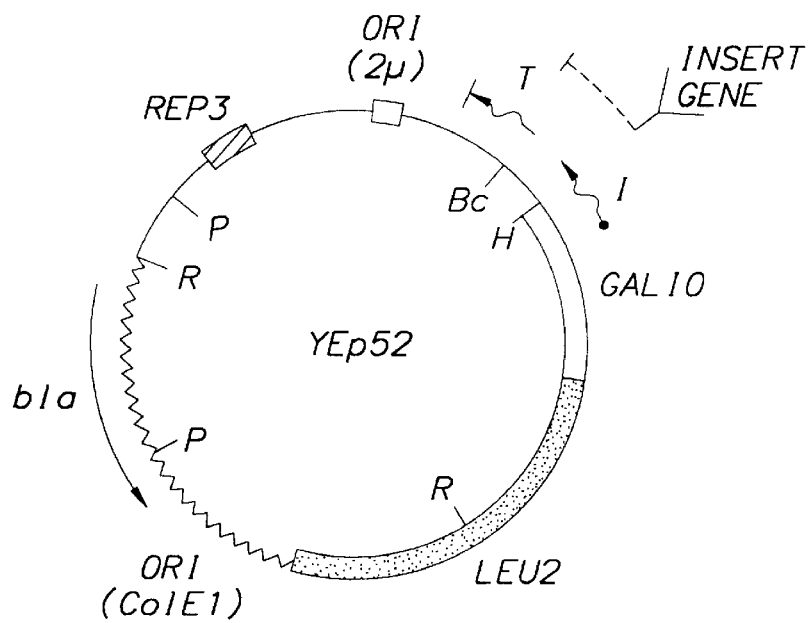

Retron-Ec67 was prepared from plasmid pCL-1BPv4 in which the 4-kb BalI-PvuII fragment (DNA from fragment from the BalI to 2nd PvuII site from the left end of the map depicted in FIG. 5 was cloned into the HincII site of pUC9. E. coli harboring this plasmid produced msDNA-Ec67 (Lampson et al., Science, 243, 1033–1038, 1898).

A total RNA fraction was prepared from cells transfected with pC1-1EP5c; pC1-1EP5c contains the 5-kb PstI(a)-EcoRI fragment encompassing the entire 4-kb BalI-PvuII sequence in PC1-1BPv4. See FIG. 7.

The construction of plasmid YEp521 proceeded as follows. The DNA fragment containing the pUC19 multiple cloning sites were isolated by digestion of pUC19 with EcoRI, the cleaved ends were filled in with the Klenow fragment of DNA polymerase I, and then digested with HindIII. The resulting 54-bp fragment was cloned into YEp52 by replacing a fragment between the BclI (filled in with the Klenow fragment) and HindIII sites, resulting in YEp521.

YEp521, thus constructed, contains the multiple cloning sites from pUC19, except for EcoRI, downstream of the GAL10 promoter.

The 4-kb HindIII-BamHI fragment from pC1-1BPv4 (see FIG. 7) was cloned into the HindIII and BamHI sites of YEp521.

As a result, the msr-msd region and the RT gene of retron-Ec67 were placed downstream of the GAL10 promoter. This plasmid is designated YEp521-M1.

Plasmid YEp521-M1 is illustrated in FIG. 7. The shade bars are the regions inserted in yeast vector, YEp521.

It will be noted that the RT of retron-Ec67 gene is located behind (downstream) the msr-msd region.

2. Production of msDNA in transfected yeast. A yeast strain (SP1, a vra3 leu2 trp1 his3 ade8 can gal2) was used. Transfection of the yeast cells was carried out by the lithium acetate method of (Ito et al., J. Bacteriol., 153, 163–168, 1983). Yeast culturing was carried out as described below. msDNA was produced and was detected by extending the 3' end of msDNA by avian myeloblastosis virus reverse transcriptase (AMV-RT). This yielded a main product of 117 nucleotides. Treatment of this product with ribonuclease A resulted in a DNA of 105 nucleotides. These results are in good agreement with the structure of msDNA-Ec67. (See Lampson et al., Science, 243, 1033–1038, 1989). The production of msDNA-Ec67 was further conformed by Southern blot hybridization.

To determine whether the production of msDNA-Ec67 could occur in yeast without the RT genes from retron Ec67, the following work was performed.

An RNA preparation from cells harboring YEp521-M2 only contains the msr-msd region under the GAL10 promoter, and described herein above (See FIG. 7) was analyzed by Southern blot hybridization. As shown in lane 2, FIG. 9, no band corresponding to msDNA-Ec67 was detected, indicating that the RT gene from retron-Ec67 is essential for the msDNA synthesis in yeast cells.

In a similar manner, CHO cells can be transfected using known strategies and techniques. The same could be done with HeLa cells, COS cells, or other vertebrate mammalian cells.

Gene Rearrangement in Retrons. An important finding in connection with the invention is that the yield of msDNA in transfected yeast cells is significantly improved by means which cause, it is believed, an increase in production of RT. One such strategy is to reduce by as many as possible the numbers of the AUG codons between the transcriptional initiation site of the GAL10 promoter (or any other promoter used for that purpose) and the initiation codon of the RT gene. Best results were obtained when a portion of the 5' end non-coding region containing initiation translation codons AUG is deleted, but for the first AUG codon in closest proximity to the 5' end.

Thus, it was found that a significant portion of the 5' end of the non-coding region was not essential to production of msDNA in yeast cells. Deletion of a portion of the nucleotide sequence containing the AUG codons significantly improved the yield of msDNA production.

Specifically in YEp521-M1 (See FIG. 7), there are 417-bp from the 5' end HindIII site to the initiation codon GAA for RT. (See FIG. 7 in Lampson et al., Science, 243, 1033–1038, 1989). A deletion of the 240-bp sequence upstream of the msr gene from the left hand most HindIII site to immediately upstream of msr of YEp521-M1 (See FIG. 7) was carried out.

For this purpose, the fragments of 140-bp msr-msd (including 5 extra bases upstream of msd and 18 extra bases at the 3' end of the msr-msd region upstream of msd) (after PCR amplification) and the 1.8-kb RT gene (including 8 bases upstream) of the initiation codon of the RT gene (also after PCR amplification) (and 4 bases downstream of the termination codon), were cloned into the HindIII and BamHI sites of YEp521-M1 yielding YEp521-M3 (See FIG. 7). The yield of msDNA-Ec67 in transfected yeast with YEp521-M3 was shown to be significantly increased, as discussed below.

Another important finding made to substantially increase the yield of msDNAs in yeast is to transpose the position of the RT gene with respect to the msr-msd region. In bacterial retrons, the msr-msd region is in front of the RT gene; when the RT was moved upstream of the msr-msd region, a further increase in yield of msDNA was observed. This was accomplished as follows.

Since the msr-msd region of YEp521-M3 still contains 3 AUG codons, YEp521-M4 (See FIG. 7) was constructed, in which the order of the RT gene and the msr-msd region was reversed, i.e., the msr-msd region being positioned after the RT gene. In YEp521-M4, there is only one AUG codon between the left hand-most HindIII site and the BamHI site (See FIG. 7), which exists in the multiple cloning sites of PUC19. (Yabisch-Perron et al., Gene, 33, 103–119, 1985). This AUG codon is terminated by a termination codon, UAG after 5 codons. The initiation codon, GAA, for the RT gene was placed 6 codons after the termination codon in the same reading frame.

YEp-M5 was then constructed from YEp521-M4 by adding 50-bp antisense DNA for cdc28 into the region coding for msd (described in further detail below). Therefore, two plasmids were constructed in which the order of the RT gene and the msr-msd region was reversed.

The yield of msDNA-Ec67 in transfected yeast cells with YEp521-M4 was compared between YEp521-M4 and YEp521-M3. This gene rearrangement brought about a further increase of yield over YEp521-M3. The msDNA production was increased approximately 1.2 and 9.4-fold with YEp521-M3 and YEp521-M4, respectively, over YEp521-M1.

It has been reported that a ribosomal subunit (carrying Met-trNA$^{met}$ and various initiation factors) binds initially at the 5' end of mRNA and then scans through the mRNA stopping and then initiates translation at the first AUG codon in a favorable context (Kozak, J. Cell Biology, 108, 229–241, 1989). From a recent survey of 699 vertebrate mRNAs, GCCGCCaCCAUG emerges as the consensus sequence for initiation of translation in higher eucaryotes (Boeke et al., Cell, 40, 491–500, 1985). The survey reports the study of the 5' non-coding sequences of the 699 vertebrates mRNAs (all sequences to which access could be had in the literature). The mRNA source of the vertebrates included human, (muscle, skeletal, liver, intestinal, etc.) bovine, rat and others. Also in yeasts, AUG was reported to be the consensus of sequence for initiation of translation. (Hamilton et al., Nucl. Acids Res., 15, 3581–3583, 1987) It is noted that Kozak, J. Cell Biology, 108, 229–241, 1989 also reported variations and exceptions to the more general rule described above. For instance, there are reported cases where initiation is not restricted to first AUG codon, which therefore is not used exclusively, but includes other AUG codons in the vicinity of the 5' end. Further, inactivating the first AUG codon closest to the 5' end, allowed ribosomes to initiate translation at another codon (UUG).

As described herein above, the location of the initiation codon of the ORF for various msDNAs can vary (e.g., 19-bp from the start of the msd gene for Ec86 retron and 77-bp for the Mx162 retron). Thus, one skilled in the art can adjust the length of the excised non-coding region of the retron when the above strategy is followed.

The finding in connection with the invention described above, namely, that a significant improvement in yield of msDNAs takes place when AUG codons between the transcriptional site of the GAL10 promoter and the initiation codon of the RT gene are deleted, but for the one AUG codon closest to the 5' end which is preserved, is therefore consistent with the above-discussed literature reports. Accordingly, this finding made in accordance with the invention with respect to the production of msDNAs is not intended to be limited to yeast, but can reasonably be predicted to apply to other msDNA-producing transfected eucaryotes, in particular higher eucaryotes like mammalian cells, e.g., HeLa cells, CHO, COS-1 cells and others.

The same observation can be made regarding the position of the RT gene upstream of the msr-msd region. This finding too is believed to have general applicability to the production of msDNAs in eucaryotes, as noted above. It is believed that these described strategies may contribute to an increase in RT and ultimately in yield of msDNAs.

It will be apparent to one skilled in the art that the two strategies described (deletion of AUG codons and inversion of the respective positions of the RT gene and the msr-msd region, do not have to be performed together (as shown with respect to YEp521-M4), which is a best mode to date. For instance, the strategy may be performed without the deletion strategy, and vice-versa. Further, as noted above, any strategy which will contribute to the increase of the production of RT, is considered within the scope of the invention.

The msDNAs which are synthesized from these new retrons are also new.

As has been noted herein, it is not necessary that one promoter for the RT gene and the msr-msd region be used. More than one can be used, one for the RT and one for the msr-msd region. When it is desired to use two promoters, either one or both of the strategies to increase RT production namely the inversion and/or deletion strategy can also be used, as will be apparent to on e skilled in the art.

It is noteworthy that the DNA sequences, which contain these unique retrons (due to the deletions and/or position inversion) and which encode the new msDNAs, are new when compared to known bacterial retrons. So are the replicating vehicles carrying these retrons and the transfected eucaryotes harboring these vehicles. They provide effective means to produce new single-stranded DNA in eucaryotes in improved yields.

It is to be noted also that the two above-described strategies which have been discussed with respect to eucaryotes are applicable to msDNAs produced from modified retrons in procaryotes.

The invention has been illustrated with an illustrative retron, Ec67. However, by a similar procedure, yeast can be made to produce other msDNAs. For instance, in a similar manner, retron Ec73 can be used to transfect yeast strain SP1 to produce msDNA-Ec73.

Likewise, a similar procedure can be followed to transfect and produce msDNA-Mx65in yeast from the necessary retron elements. See Dhundale et al., *JBC,* 263, 9055–9058, 1988. Its ORF codes for 427 amino acid residues.

If it is desired to produce msDNA-Mx162 in yeast, the appropriate DNA fragment containing retron Mx162can be prepared from a 17.5-kb Sal1 fragment which is disclosed in Yee et al., *Cell,* 38, 203–209, 1984. Its ORF codes for 485 amino acid residues.

For the expression of msDNA-Ec107, a similar strategy may be followed. The retron is a 1.3-kb DNA fragment of which the 34-bp intergenic sequence between pyrE and ttk (in FIG. 4) is deleted. The retron contains an ORF coding for 319 amino acid residues (from base 396 to 1352 in FIG. 2). The reference to Figures made hereinabove is to Dhundale et al., *Cell,* 51, 1105, 1987. This retron is the smallest yet found in bacteria.

The retron for Sa163 was determined to be contained in a 480-bp DNA fragment encompassing the msd and msr regions (Furuichi et al.).

The retron for Ec73 was determined to be contained in a 3.5-kb SalI(b)-EcoRI(c) fragment. See FIG. 1A of Sun et al.. For details on Ec73, see below.

The retron for Ec86 was determined to be contained in a 3.5-kb PstI fragment (Lim and Maas, *Cell,* 56, 891–904, 1989).

Likewise, from retrons Sa163, Ec86 and Ec73, the corresponding msDNAs, msDNA-Sa163, msDNA-Ec86 and msDNA-Ec73 may be produced in transfected yeast cells. If plant or mammalian vertebrate cells are used, appropriate manipulations and strategies will be followed.

Similar techniques may be followed to express other msDNAs known or yet to be found or to be synthesized from their respective retrons. All of these retrons are expected to contain the elements necessary to synthesize the unique features of msDNAs, as is described herein.

Thus, in general retrons containing the essential features described herein are useful to produce in vivo in eucaryotes the stable (not degraded) msDNAs having the conserved and characteristic features described herein.

msDNA-Ec73 is synthesized from retron Ec73 which is described in Sun et al., *Journal of Bacteriology,* 173, 4171–4181, 1991. This reference is incorporated by reference. FIG. 2 therein shows the nucleotide sequence capable of synthesizing msDNA-Ec73, a 3.5-kb S(b)-E(c) fragment. It was determined that the first ATG codon at position 11,544 is the initiation for the necessary RT gene and the ORF for the RT is of 316 residues.

It is to be noted that in all retrons known to date, the RT gene is located at 20 to 77-bp upstream of the msd gene (downstream of the msd gene).

In all retrons studied to date, it is believed that the promoter elements serve as the promoters for both msdRNA synthesis and the RT from the ORF. For instance, for msDNA-Ec67, promoter elements in a −10 region TTGACA and in a −35 region TGAAT, are believed to fulfill this function. See Lampson et al., *Science,* 243, 1033–1038, 1989. However, in accordance with the invention, it is not essential that there be one promoter element for both components, but rather two promoter elements, one for initiating RNA polymerase transcription for the RT gene and the other for the msr-msd region. Thus the msr-msd region and the RT gene can be expressed under two independent promoters, which would be likely to complement each other. However, it appears at this time that at least for two of the msDNAs described herein (msDNA-Ec67 and msDNA-Ec73), the production of msDNA-Ec67 can only be complemented by the RT-Ec67 and not by the RT-Ec73 or vice-versa.

Further, it is often desired to use a strong promoter rather than the native promoter.

Another important embodiment of the invention relates to the in vivo production in eucaryotes of any DNA fragment (s), non-native or foreign, to the msDNA structure. Likewise, the vectors and the transfected eucaryotic hosts, carrying such foreign DNA fragment(s) are encompassed by the invention. The invention thus makes possible the synthesis in vivo in eucaryotes of stable msDNAs which encompass a foreign DNA fragment in the DNA portion or a foreign RNA fragment in the RNA portion of the DNA-RNA hybrid structure. Of particular interest are msDNAs which include a single-strand DNA or RNA fragment which is complementary to the mRNA of a particular target gene (or fragment thereof) (antisense DNA or RNA). The antisense fragment may be the loop or may be part of the loop of the secondary structure of the msDNA.

In one example of this embodiment, there was constructed a plasmid, YEp521-M5, into which there was inserted in the msd region, nucleotides 299–426 of YEp521-M4 (the boxed region of the lower strand of FIG. 7 of Lampson et al., *Science,* 243, 1033–1038, 1989), a XhoI restriction recognition site (T↓CTAG)); a foreign DNA fragment of 50bp was inserted in this XhoI site. YEp521-M5 was transfected into yeast (SP-1) and the subsequently expressed msDNA designated herein as msDNA-Ye117 (see FIG. 2B).

In a like manner, there may be inserted into the msr region of YEp521-M4 a restriction recognition site, and into a DNA fragment. This retron may be transfected into yeast (SP-1), and the subsequently expressed msDNA is a new structure. It corresponds to the structure designated here as msDNA-Ye117, except that the new foreign fragment is in the RNA portion of the msDNA.

The invention makes possible the construction of a system that may be used to regulate the production of genes. The modified msDNAs of the invention contain in the DNA portion, a cloned DNA fragment from a gene downstream of a promoter in the orientation promoting the production of antisense DNA or RNA (micRNAs). The "micRNA" terminology has been applied to an RNA transcript which is an mRNA-interfering-complementary RNA (Coleman et al., *Cell,* 37, 429–436 (1984) and literature references cited therein). "micRNA" has been reported to inhibit the production of certain proteins (e.g., OmpF). A similar regulation has been reported for a micRNA and the gene for the Tnl0 transposase gene. The gene for the micRNA and for the transposase are reported to be transcribed in opposite directions off the same segment of DNA, such that the 5' ends of their transcripts can form a complementary hybrid. The hybrid is thought to inhibit the translation of the transposase mRNA. Coleman et al., supra., report the construction of an artificial "mic" system designed to regulate the expression of any specific gene in *E. coli*.

Various cell division cycle (cdc) genes are known; by now some 50 different cdc genes have been defined in terms of landmark events occurring during duplication of cellular molecules (e.g., glycolic events). Various cdc genes and their functions are described in Watson et al., *Molecular Biology of the Gene,* Fourth Ed. (1987), Chapter 18. Amongst these are cdc4 required for initiation of DNA synthesis in the mitotic cell division cycle and other functions; cdc7 of similar function to cdc4 but for premeiotic DNA synthesis; cdc28 necessary for duplication of the spindle pole body is homologous to mammalian protein kinases and has protein kinase activity, and others like cdc8, cdc9 and others.

The strategy to produce a msDNA containing a foreign dsDNA fragment in its DNA portion is depicted in FIG. 10. The DNA fragment is shown (dark bar). The 50-bp nucleotide fragment is shown below with 5'TCGATGTAATTTGCTAATTCACCGCTCATGTTCGAAGG-
ATAGTTCTATTTGATC3'ACATTAAACGATTAAGTGGCG-
AGTACAAGCTTCCTATCAAGATAAACTAGAGCT5'

Yeast cells (SP-1) transfected with YEp521-M5 produced a new msDNA-like structure, msDNA-YE117, shown in FIG. 2B (analyzed by polyacrylamide-urea gel electrophoresis). This new msDNA construct contains the 50-bp DNA fragment. It is contemplated that the new msDNA is a useful vector for antisense DNA. The size of the antisense DNA fragment may be from 4 bases in length or longer, for example 4 to 30 or 4 to 100 bases in length. The new construct is expected to produce a single stranded DNA which is complementary to a specific mRNA, in this instance, that of cdc28 and inhibit the expression of that mRNA, and of the gene.

Antisense DNA (micDNA) and micRNAs which are complementary to regions of the mRNA known to interact with ribosomes, would be of particular interest. Hence, such msDNAs are those that contain such DNA-micDNA generating regions are of special interest for various applications. Thus, by inserting an appropriate DNA fragment of a gene after a promoter, e.g., into an XhoI site, one can construct with the msDNAs disclosed herein (and others) a system to specifically regulate the expression of any gene.

This is the first time that such antisense system has been provided from a molecule produced in an eucaryote.

It is contemplated that other DNA fragments be inserted in the msd region and/or the msr region of the plasmid here disclosed and the corresponding new msDNAs synthesized which may have similar functions, e.g., to generate a micDNA or a micRNA complementary to a mRNA to inhibit its gene.

Likewise, YEp521-M1 can be modified, producing an enlarged new msDNA structure (on the 5' end of the DNA portion of msDNA).

When it is desired to insert a DNA sequence encoding a protein (polypeptide) e.g., two copies of a gene, the DNA sequence will be inserted in opposite orientation to another at a selected restriction site into the msd sequence of an msDNA of choice, such as YEp521-M4. There is expected to be produced in an eucaryotic host, a novel msDNA-RNA structure. When the lacZ gene is incorporated into a suitable location in the msd region of the selected construct, it is expected that β-galactosidase activity will be detected.

EXAMPLES

The following Examples are offered by way of illustration and are not intended to limit the invention in any manner. In these Examples, all percentages are by weight for solids and by volume for liquids, and all temperatures are in degrees Celsius unless otherwise noted.

For convenience and clarity, the Examples refer to and provide also a detailed description of the Figures.

EXAMPLE 1

Yeast Strains, Media and Growth Condition

Yeast SP1 strain (a ura3 leu2 trp1 his3 ade8 can$^r$ gal2) was used. Cells were grown in YPD medium (1% yeast extract, 2% bactopeptone, and 2% glucose). For screening transformants of YEp52 and its derivatives, a minimal medium was used (Rose et al., *Methods in Yeast Genetics: A Laboratory Course Manual,* Cold Spring Harbor Lab., Cold Spring Harbor, N.Y., 1990) supplemented with all nutrients required but leucine. For galactose induction, 0.15 ml of the pre-cultured cells in the minimal medium containing 2% galactose instead of glucose were utilized. The cells were grown at 30° until late-log phase. Yeast transfections were carried out by the lithium acetate method (6). Transfection of yeast cells was confirmed as follows: the plasmid prepared from yeast transformants was transfected into *E. coli* DH-5 (F$^-$endA1 recA1 hsdR17 (rk$^-$,k$^+$) supE44 thi-1, gyrA96, relA1) and the plasmid prepared from DH-5 cells was not yet subsequently characterized. Plasmid DNA from yeast cells was prepared according to the method described by Hoffman and Winston, *Gene,* 57, 268–172, 1987.

Plasmids

YEp52 (Broach et al., *Experimental Manipulation of Gene Expression,* Academic Press Inc., New York, 1983) was used to construct plasmids for expression of msDNA in yeast. This plasmid contains the ColE1 origin of replication, a promoter of the GAL10 gene, LEU2, the 2μ-circle origin of replication, and the 2μ-circle REP3 locus. Retron-Ec67 was prepared from plasmid pC1-1BPv4 in which the 4-kb Ba1I-PvuII fragment (DNA fragment from the Ba1I to the 2nd PvuII site from the left end of the map described in FIG. 5 of Lampson et al., *Science,* 243, 1033–1038, 1989), was cloned into the HincII site of pUC9. *E. coli* harboring this plasmid produces msDNA-Ec67. A total RNA fraction was prepared from cells transfected with pC1-1EP5c. pCL-1EP5c contains the 5-kb PstI(a)-EcoRI fragment encompassing the entire 4-kb Ba1-I-PvuII sequence in Pc1-1BPv4 (see FIG. 5 of Lampson et al., *Science,* 243, 1033–1038, 1989) in pUC9.

Plasmid Construction

Plasmid YEp521 was constructed by introducing the multiple cloning sites of pUC19 (Yanisch-Perron et al., *Gene*, 33, 103–119, 1985) into YEp52 (Broach et al.,*Experimental Manipulation of Gene Expression*, Academic Press Inc., New York 1983), which was designed to obtain high-level, inducible expression of a cloned gene under the GAL10 promoter in yeast. The DNA fragment containing the pUC19 multiple cloning site was isolated by digestion of pUC19 with EcoRI; the cleaved ends were filled in with the Klenow fragment of DNA polymerase I, and then digested with HindIII. The resulting 54-bp fragment was cloned into YEp52 by replacing a fragment between the BclI (filled in with the Klenow fragment) and HindIII sites, resulting in YEp521. YEp521, thus constructed, contains the multiple cloning sites from pUC19, except for EcoRI, downstream of the GAL10 promoter. The 4-kb HindIII-BamHI fragment from pC1-1BPv4 was cloned into the HindIII and BamHI sites of YEp521. As a result, the msr-msd region and the RT gene of retron-Ec67 were placed downstream of the GAL10 promoter. This plasmid is designated YEp521-M1 as shown in FIG. 7.

In order to eliminate a fragment of 242 bases upstream of msr which contains several ATG codons, polymerase chain reaction (PCR) was performed using YEp521-M1 as a template with two synthetic oligonucleotides, M2-a (5'GCAAGCTTCATAAACACGCATGT3') and M2-b (5'CTGGATCCAGAAACGCATGCAGG3') as primers. These sequences correspond to the sequences from base 243 to 258 of retron Ec67 for M2-a and from base 384 to 369 for M2-b (see FIG. 7 of $^{22}$), which flank the msr-msd region. The 140-bp PCR product was gel-purified and digested with HindIII and BamHI. The resulting fragment was cloned into the HindIII and BamHI sites of YEp521, yielding YEp521-M2. YEp521-M2 contains only the msr-msd region under the GAL10 promoter.

To insert the RT gene at the BamHI site of YEp521-M2, the 1.8-kb BamHI fragment encompassing the RT gene was amplified by PCR using YEp521-M1 as a template and two oligonucleotides, M3-a (5'CTGGATCCAAGAAATGACAAAAACA3') and M3-b (5'CTGGATCCTTCATTAGCTATTTAACAT3') as primers, which correspond to base 409 to 429 and from base 2182 to 2163 of retron-Ec67 (see FIG. 7 of Lampson et al., *Science*, 243, 1033–1038, 1989), respectively. The 1.8-kb fragment was gel-purified, digested with BamHI, and closed into the BamHI site of YEp521-M2. The resulting plasmid was designated YEp521-M3.

YEp521-M4 was constructed to change the order of the msr-msd region and the RT gene. The msr-msd region was amplified by PCR using M2-a and M2-b (see above) except that SmaI sites were added at their 5' ends. The 1.8-kb BamHI fragment containing the RT gene was cloned into the BamHI site of YEp521. Subsequently, the 140-bp SmaI fragment containing the msr-msd region was cloned into the SmaI site of the above plasmid and resulting plasmid was designated YEp521-M4.

YEp521-M5 was constructed from YEp521-M4 to add the 50-bp antisense DNA for cdc28 (XhoI fragment) into the msd region. The XhoI site was added into the msd region of YEp521-M4 by PCR. This construct was then digested by XhoI; then the antisense DNA was ligated to the msd region of retron Ec67. This plasmid was transfected into yeast (SP-1) and the subsequently expressed msDNA designated herein as msDNA-Ye117.

Detection of msDNA

A total RNA fraction from yeast cells was prepared as described by Elder et al., *Proc. Natl. Acad. Sci. USA,* 80, 2432–2436, 1983 and a total RNA fraction from *E. coli* was prepared from *E. coli* harboring pC1-1EP5c by the method described by Chomzynski et al., *Anal. Biochem.*, 162, 156–159, 1987.

To label msDNA with reverse transcriptase, the total RNA fraction prepared from 0.9 ml of a late-log culture was added to 20 µl of a reaction mixture containing 30 mM Tris-HCl (pH 8.2), 50 mM KCl, 10 mM MgCl$_2$, 5 mM DTT, 0.2 mM each of dTTp, dGTP, dCTP, 5 µCi of [γ-$^{32}$P]dATP and 5 units of avian myeloblastosis virus reverse transcriptase (AMV-RT; Molecular Genetic Resources). The reaction mixture was incubated at 30° C. for 1 hour, and an aliquot of the reaction mixture was subjected to electrophoresis with a 6% polyacrylamide –8M urea gel. Another aliquot was treated with RNase A (10 µg/ml) for 10 minutes at 37° C. and subjected to electrophoresis.

msDNA-Ec67 was also detected by Southern blot analysis (Southern, *Mol. Biol.,* 98, 503–517, 1975). Total RNA from 2.5 ml of a late-log culture was applied to a 1.5% agarose gel with E buffer [40 mM Tris HCl (pH 8.0), 10 mM sodium acetate, 2 mM EDTA]. After electrophoresis, the gel was blotted to a nylon membrane filter (PALL BLODYNE A TRANSFER MEMBRANE; ICN) by the capillary transfer method. Hybridization was carried out in 50% (v/v) formamide, 5×SSPE [1×SSPE; 180 mM NaCl, 10 mM sodium phosphate (pH 7.4), 1 mM EDTA], 0.3% sodium dodecyl sulfate, and 5×Denhardt's solution (Denhardt, *Biochem. Biophys. Res. Commun.,* 23, 641–646 (1966)) with the nick-translated 140-bp msr-msd region as a probe (Rigby et al., *J. Mol Biol.*, 113, 237–251, 1977).

As noted above, the invention provides for the expression of the desired msDNAs from eucaryotes in general. While the invention is illustrated with a yeast of the genus Saccharomyces, other eucaryotes are readily suitable to practice the invention.

A convenient source of suitable yeasts is found in the *ATCC Catalogue of Yeasts,* 18th Ed., 1990. Because of practical and economic importance, the invention is particularly directed to the genus Saccharomyces which is extensively used in baking, beer, wine and other industries. Conventionally these yeasts are referred to as baker's, brewer's and wine yeasts.

Amongst these, of special interest are the *S. cerevisiae* strains, the *S. bayanus, S. carlsbergenensis, S. diataticus,* and *S. uvarum,* which lend themselves to transfection with the vectors of the invention. Further, to express the msDNAs, one may use vertebrate host cells like COS-1, CHO and HeLa cells or in vertebrate cells or plant cells.

Plants that may be used include monocotyledons and dicotyledons. Illustrative examples of plants which may be transfected are the following: alfalfa, soybeans, maize and wheat. *Genetic Engineering of Plants, An Agricultural Perspective,* Edited by Kosuge et al., Plenum Press (1983).

To carry out the present invention, various cloning vectors may be used to transfect compatible eucaryotic host cells for replication of the vector. Thereafter the transformants are identified, plasmid DNA prepared therefrom, and the msDNAs extracted and purified.

Vectors for expression of cloned genes in yeasts are described in *Methods in Enzymology*, Vol. 194, "Guide to Yeast Genetics and Molecular Biology", page 373 (Guthrie and Fink, Eds., Academic Press Inc., 1991). It will be apparent from one skilled in the art to select an appropriate promoter for expressing msDNAs in yeast with or without a foreign DNA fragment, such as from regulatable promoters of the GAL family, e.g., GAL4, GAL80, GAL1, GAL2, GAL7, GAL10, GAL11, MEL1; ADH1 and PGK; also see Broach et al., *Experimental Manipulation of Gene Expression,* Academic Press, Inc., New York, 1983 or non-regulatable strong promoters.

Oligonucleotide synthesis may be carried out by a number of methods including those disclosed in U.S. Pat. No. 4,415,734, and in Matteuci et al., *J. Am. Chem. Soc.,* 103 (11):3185–3191 (1981), Adams et al., *J. Am. Chem. Soc.,* 105 (3):661–663 (1983), and Bemcage et al., *Tetrahedron Letters,* 22 (20):1859–1867 (1981).

For the expression of msDNAs in higher eucaryotes with or without selected DNA fragment, one skilled in the art may refer to and use known techniques. The advantages of synthesizing particular eucaryotic proteins in eucaryotes are well known. Depending on the msDNA which is intended to be produced, an appropriate eucaryote host cell will be selected. See *Molecular Cloning: A Laboratory Manual,* Second Edition, §3, §16.3 and seq. (Sambrook et al., Cold Spring Harbor Laboratory Press, 1989). The eucaryotic expression vehicle will contain, as is known, a promoter and enhancer elements, recognition sequences, the TATA box and upstream promoter elements. Other conventional elements located upstream of the transcription initiation site for replication and selection are known and described in standard laboratory manuals. Vectors are available commercially, for instance from Pharmacia pMSG, pSVT17, pMT2). For methods for introducing recombinant vectors into mammalian cells, see *Molecular Cloning: A Laboratory Manual,* Second Edition, §16.30–16.55, (Sambrook et al., Cold Spring Harbor Laboratory Press, 1989). For cosmid vectors for transfection of mammalian cells, see *Molecular Cloning: A Laboratory Manual,* Second Edition, §23.18 and seq., (Sambrook et al., Cold Spring Harbor Laboratory Press, 1989).

Further, one skilled in the art may wish to refer to *Current Protocols In Molecular Biology,* Volume 1, §16.12–16.13.7 (Ausubel et al., Eds., Greene Publishing Associates and Wiley-Interscience, 1989), discussing in particular, three vector systems or strategies for introducing foreign genes into mammalian cells with COS cells, CHC and vaccinia viral vectors. One skilled in the art will select the most appropriate system for the production of msDNAs from the selected retrons. Further, for introduction of DNA into mammalian cells. See *Current Protocols In Molecular Biology,* Volume 1, §9.01–9.93 (Ausubel et al., Eds., Green Publishing Associates and Wiley-Interscience, 1989).

By conventional known methods, a foreign DNA strand which is complementary to an mRNA of a target gene can be inserted into a retron before transfection of a eucaryotic plant or animal cell. The foreign DNA fragment encodes an antisense RNA or DNA.

One suitable method for introduction of a foreign nucleic acid sequence into a retron is by restriction enzyme cleavage of the msDNA and directional cloning of the foreign sequence. By selecting an msDNA of known or partially known sequence, such as msDNA from *E. coli* (such as Ec67 or Ec73), *Myxococcus xanthus* (such as Mx162 or Mx65), or *Stigmatella aurantiaca* (such as Sa163), or by synthesizing an msDNA to control the sequence of bases, one or more appropriate restriction enzymes may be selected. Preferably, a restriction enzyme is used which will cleave the retron in a region that will generate a loop in the stem portion of the msRNA or the msdDNA portion of the msDNA. Since the msDNA molecule generally contains more than one secondary structure with a loop, at least two inserts can be incorporated if desired, one in each loop. Thus, it is possible to target two or more different gene products with one msDNA vector. Alternately, for applications other than antisense, the cleavage may be at any available restriction site in the msDNA molecule, other than being solely in the regions encoding the loop. The foreign DNA fragment is ligated into the restriction enzyme cleavage site. Suitable methods for introduction of foreign nucleic acid fragments are taught in Ausubel, et al., *Current Protocols in Molecule Biology,* John Wiley & Sons, Inc., and in Sambrook, et al., *Molecular Cloning: A Laboratory Manual,* 2d ed., Cold Spring Harbor Laboratory Press, both of which are incorporated herein by reference.

Transfection of eucaryotic cells, including both animal and plant cells, with a retron for msDNA is accomplished by conventional means, e.g., lipofectin, calcium phosphate, electroporation, or microinjection of the retron into the target cell. By microinjection, the retron will integrate into the host cell genome or the mRNA transcribed from the retron which in the presence of RT will generate the msDNA. In the latter protocol, the RT gene will have been introduced separately into the vector. The retron mRNA may be synthesized in vitro by means of a suitable vector containing the retron under control of a phage promoter, such as SP6, T7, or T3. An additional method is transfection of cells with a retrovirus vector. The above methods, and other suitable methods of transfecting eucaryotic cells, are taught in Ausubel, and Sambrook, supra.

EXAMPLE 2

Production of msDNA in Mammalian Cells

Plasmid Construction

To construct the expression plasmid for msDNA synthesis, plasmid YEp521-M1 was used as a source of the RT coding region. An NcoI site was first introduced into the 5'-end of the RT gene carried on YEp521-M1 by polymerase chain reaction (PCR). The two oligonucleotides used were 5'-CTCTCCATGGTTAAAACATCTAAACTT-3' and 5'-TAAAGCTTTCAAAAAAATCCTTAA-3', which correspond to bases 418–438 and 779–802, respectively, of the retron sequence and contain NcoI and HindIII sites, respectively. Thirty PCR cycles were performed using Taq polymerase (Perkin-Elmer) according to the manufacturer's recommendation. After the PCR reaction, the product was digested with NcoI and HindIII. To create an XbaI site at the 3'-end region of the RT gene, the HindIII-BamHI fragment of the RT gene from YEp521-M1 was cloned into the pBluescript SK vector (Stratagene Inc.) resulting in pBRT. The 0.39-kb NcoI-HindIII PCR fragment was then ligated with the 1.43-kb HindIII-XbaI fragment obtained from the pBRT plasmid. The ligated fragment was then inserted between the NcoI and XbaI sites of pEMCLucβgAn (Deng, et al., *Gene,* 109:193–201 (1991)) in order to replace the coding region of the luciferase gene with that of the bacterial RT gene. pEMCLucβgAn also contains a promoter for T7 polymerase, the EMCV region and a 3' β-globin untranslated region (UTR) with the $dA_{23}dC_{30}$ sequence (βgAn) from *Xenopus laevis*. This resulted in plasmid pERT with the RT coding region under the control of the T7 polymerase promoter and in the same reading frame as the 11th AUG codon of EMCV.

To construct plasmid pERTMS, which can produce msDNA-Ec67, the pCRT plasmid, containing the HindIII-BamHI fragment with the RT coding region followed by the msr-msd region, was inserted into the pCDNAneo vector (Invitrogen, Inc.). The msr-msd region, with a small 3'-part of the RT was cut out by PstI and cloned into the 3'-end of the RT gene in the pERT plasmid.

Cell Culture and Transient Transfection

Mouse NIH3T3 cells (clone 3126-2, Ref. 8) were grown in Dulbecco's modified Eagle's medium (Life Technologies, Inc.) supplemented with 10% fetal bovine serum (Hy-Clone Laboratories Inc.) at 37° C. in a 5% $CO_2$ environment. Transfection was performed with Transfectam reagent (Promega Inc.) $1.5 \times 10^6$ cells were plated onto 100-mm² dishes 24 h before transfection, which resulted in approximately 75% confluency at the time of DNA exposure. Transfections were performed in serum-free Dulbecco's modified Eagle's medium at a Transfectam:DNA ratio of 2 μl of Transfectam to 1 μg of DNA. The DNA-Transfectam mixture was overlaid onto the cells for 6–8 h. The medium was aspirated and replaced by regular medium without washing. Confluent plates were harvested at 48 h post-transfection for determination of msDNA production.

Other msDNAs are produced in eucaryotic cells transfected with selected retrons by the method described in Example 2. The retrons are similar or identical to those described herein and in the literature or are synthesized. The retrons which are suitable are those which can synthesize msDNAs in conjunction with a reverse transcriptase which is capable of transcribing the RNA portion of the msDNA (as described earlier herein). The msr and msd genes may also be synthetically generated from pairs of oligonucleotides, as is known, to generate, with a selected RT, msDNAs which are synthetic since both components—the DNA and the RNA—of the hybrid molecule are synthetically generated as opposed to being isolated from a prokaryotic source. In the retrons, the gene for RT may be upstream or downstream of the genes for msr and msd. Any eucaryotic cell capable of being transfected with a vector harboring a foreign nucleic acid fragment, may be transfected to produce msDNA in this manner.

Plant cells may be transfected to produce msDNAs. Several suitable methods are known for the transfection of plant cells, which methods may be used to transfect a plant cell with a retron. See Ausubel, supra, Unit 9.3 One such method is the use of Agrobacterium cells, such as *Agrobacterium tumefaciens* or *Agrobacterium rhizogenes*, carrying in a vector, such as a binary vector or pGV3850 vector which may contain the 35S promoter of cauliflower mosaic virus, an exogenous sequence encoding a retron. A suitable method of transfection employing Agrobacterium is taught in Hanson, U.S. Pat. No. 5,286,635, incorporated herein by reference. The method of Hanson is particularly well suited for use in dicotyledonous plants. Another suitable method is by transfection of protoplasts with a retron by using a transfection agent, such as polyethylene glycol, polyvinylalcohol, and liposomes (such as Lipofectin), or by microinjection or electroporation. Transfection of plant cells, other than protoplasts, is preferably performed by microprojectile injection. This method is particularly well suited for monocotyledonous plants.

For methodologies applicable to plants, reference to the classic book by Koncz et al, entitled: "Methods in Arabidopsis Research" (1992), will be very useful.

Isolation of msDNA produced by transfected cells may be accomplished by conventional means known in the art. Suitable methods are taught in Ausubel, and Sambrook, supra. Also, see Rice et al, "Journal of Bacteriology", Vol. 175(13):4250–4254 (1993), incorporated herein by reference.

EXAMPLE 3

Expression of msDNA from Mammalian Cells

Assay for RT activity

In order to concentrate RT activity in the transfected mouse cells of Example 2, a microsomal fraction was obtained and used for the enzyme assay. This microsomal fraction was prepared according to the method of Deragon et al. with modifications as follows. The cells were lysed ($10^7$ cells/ml) with cold buffer containing 1% Nonidet P-40, 10 mM Tris-HCl (pH 8.6), 1.5 mM $MgCl_2$, and 100 mM NaCl. After 15 min of incubation on ice, the lysate was centrifuged for 20 min at 700×g on an equal volume (24% w/v) sucrose cushion in the lysis buffer in order to separate cytoplasmic and nuclear fractions. To remove mitochondria, the cytoplasmic fraction was centrifuged with 30 min at 12,000×g. The resulting microsomal fraction was then layered onto a glycerol step gradient (15 and 50% v/v) in 50 mM Hepes-KOH (pH 7.8), 50 mM KCl, 10 mM $MgCl_2$, 0.2 mM EDTA, and 3 mM dithiotreitol and centrifuged for 4 h at 120,000×g. The pellet was resuspended in 10 mM Hepes-KOH (pH 7.8), 50 mM KCl, 5 mM EDTA, and 3 mM dithiothreitol.

To assay the RT activity in purified fractions, 2–5 μg of total protein was added to a 50 μl reaction mixture containing 50 mM Tris-HCl (pH 7.8), 10 mM dithriothreitol, 60 mM NaCl, 0.05% Nonidet P-40, 10 mM $MgCl_2$, 0.5 μg of poly(A)-oligo(dT), and 0.1 μm [α-$^{32}$P]dTTP (3000 Ci/mmol). The final mixture was spotted onto DEAE paper (DE81, Whatman), it was washed with 5% trichloroacetic acid and counted in a liquid scintillator counter.

Detection of msDNA

To detect msDNA production in NIH3T3 cells transfected by pERTMS, the total RNA fraction from $5 \times 10^7$ cells was applied to a 1.2% agarose gel with or without ribonuclease A (RNase A, 10 μg/ml) treatment. After electrophoresis, the gel was blotted to Hybond™N (Amersham Corp.) nylon membrane using the PosiBlot™ system (Stratagene). Prehybridization was performed in 50% formamide, 4×SSC (1×SSC is 0.15M NaCl plus 0.15M sodium citrate), 5×Denhardt's solution, and 0.1% sodium dodecyl sulfate at 42° C. for 2 h. Hybridization was carried out with the 140-bp msr-msd region, which had been labeled by a primer extension reaction using the Amersham Inc. kit, as a probe. Hybridization was performed at 42° C. overnight. Hybridization filters were then washed and examined by autoradiography.

The existence of msDNA was also examined by the RT extension assay method. For this purpose, the total RNA fraction, which was thought to contain msDNA, was first isolated. The RNA fraction corresponding to the size of msDNA-Ec67 was then purified by preparative 6% polyacrylamide gel electrophoresis in the presence of 8 m urea, using msDNA-Ec67 obtained from *E. coli* as a marker. The purified RNA fraction was then labeled with MoMLV RT as follows. The RNA fraction was added to 25 μl of a reaction mixture containing 56 mM Tris-HCl (pH 8.3), 75 mM KCl, 10 mM dithiothreitol, 3 mM MgCl$_2$, 0.2 mM each dGTP, dATP, dTTP, 02. μm [α-$^{32}$P]dCTP (3000 Ci/mmol), and 100 units of MoMLV reverse transcriptase (Life Technologies, Inc.). The reaction mixture was incubated at 37° C. for 1 h and then chased with 2 μl of a dATP/dGTP/dCTP/dTTP mixture (15 mM each) for 15 min. Samples were phenol extracted and precipitated with ethanol. An aliquot of each sample was treated with RNase A (10 μg/ml), and then samples with and without the RNase A treatment were subjected to 6% polyacrylamide gel electrophoresis in the presence of 8 m urea.

EXAMPLE 4

Insertion of Antisense Fragment in msDNA

The methods described above, using the YEp521 plasmids, are used to construct vectors harboring msDNA containing foreign nucleic acid sequences acting as antisense. A retron, (bacterial or synthetic), is used for the insertion of a foreign nucleic acid fragment. A restriction enzyme site, or preferably two restriction enzyme sites for directional cloning, such as NcoI, XhoI, or EcoRI, is (are) inserted by PCR into a single stranded portion of the msd and/or msr region. The antisense fragment is digested with the restriction enzyme(s) and is then ligated into the restriction site(s) in the retron. The plasmid is transfected into a eucaryotic cell, such as a mammal, or other vertebrate, or a plant cell and the subsequently expressed msDNA containing an antisense fragment is expressed.

msDNA Ec73 was digested with NcoI to remove the entire stem-loop region of the DNA portion and replace it with a NcoI restriction site. The antisense fragment,

3'-TTAGATCTCCCATAATTATTACTTT-5' was ligated into the NcoI cleavage site.

The msDNA molecule produced, containing the foreign antisense fragment in the DNA region of the molecule, is transfected into a soybean plant by transfecting a binary vector in *Agrobacterium tumefaciens* and cocultivating soybean leaf fragments with the transfected bacteria.

Similarly, by methods described above, animal cells, such as human or other mammalian cells, are transfected with vectors containing the msDNA containing the antisense fragment.

EXAMPLE 5

In a similar manner as described above, an msDNA containing a foreign antisense fragment is generated in transfected COS cells from a retron of Mx162 which has a foreign RNA fragment in the msr gene, resulting in an msDNA with an antisense sequence of 50 bases in length in the RNA portion of the molecule.

EXAMPLE 6

In a similar manner, as described above in Example 5, an msDNA containing a foreign antisense fragment is generated in transfected HeLa cells from a retron of Ec73 which has a foreign DNA fragment in the msd gene, resulting in an msDNA with an antisense sequence of 50 bases in length in the DNA portion of the molecule.

EXAMPLE 7

In a similar manner, as described above in Examples 5 and 6, an msDNA containing a foreign antisense fragment is generated in transfected soybean protoplasts from a retron of Sa163 which has a foreign DNA fragment in the msd gene, resulting in an msDNA with an antisense sequence of 50 bases in length in the DNA portion of the molecule.

EXAMPLE 8

In a similar manner, as described above in Examples 5 to 7, an msDNA containing a foreign antisense fragment is generated in transfected maize cells from a retron of Ec73 which has a foreign RNA fragment in the msr gene, resulting in an msDNA with an antisense sequence of 50 bases in length in the RNA portion of the molecule.

EXAMPLE 9

In a similar manner, as described above in Examples 5 to 8, an msDNA containing a foreign antisense fragment is generated in transfected CHO cells from a retron containing msr and msd genes from Ec86 and RT from Ec67 which retron has a foreign DNA fragment in the msd gene, resulting in an msDNA with an antisense sequence of 50 bases in length in the DNA portion of the molecule. The production of msDNA in this manner demonstrates that, in the retron encoding for msDNA, the source of the msr and msd genes and the source of the RT may differ.

EXAMPLE 10

In a similar manner, as described above in Examples 5 to 9, an msDNA containing a foreign antisense fragment is generated in transfected pea protoplasts from a retron in which the msr and msd genes are synthetic, that is they are produced synthetically outside of an organism by known methods from oligonucleotides, described in the related patent application Ser. No. 08/503,730 entitled: NEW HYBRID MOLECULES, filed on Jul. 18, 1995. A foreign DNA sequence is in the msd portion of the retron. The RT in the retron is Ec67. This results in an msDNA with an antisense sequence of 50 bases in length in the RNA portion of the molecule.

EXAMPLE 11

In a similar manner, as described above in Examples 5 to 11, an msDNA containing a foreign antisense fragment is generated in transfected mouse cells from a retron in which the msr and msd genes are synthetic, a foreign RNA sequence is in the msr portion of the retron, and the RT in the retron is Mx65, resulting in an msDNA with an antisense sequence of 50 bases in length in the RNA portion of the molecule.

A fascinating utility that is being considered is the role that msDNAs of the invention can play on the formation of triple helix DNA, or triplex DNA with a specific duplex on the chromosome. A recent report in *Science*, 252, 1374–1375 (Jun. 27, 1991), "Triplex DNA Finally Comes of Age", highlights the timeliness of the present invention. Triplex DNA can be formed by binding a third strand to specific recognized sites on chromosomal DNA. Synthetic strands of sizes preferably containing the full complement of bases (such as 11–15 and higher), are discussed. The msDNAs of the invention with long 3' (or 5') ends (and the loop of non-duplexed bases) would appear to be excellent candidates. These regions provide single-stranded DNA necessary for the triplex formation. The resulting triplex DNA is expected to have increased stability and usefulness. New therapies based on the triple helix formation, including in AIDS therapy and selective gene inhibition and others are proposed in the Report.

Artificial, synthetic msDNAs can be designed that are vectors for antisense DNAs, and/or RNAs and/or ribozymes using the single-stranded DNA or RNA region of msDNAs. Such msDNA (containing a foreign ssDNA or ssRNA fragment) for use as antisense system, has been described above. The production of an msDNA with complementarity with a gene (or portion) thereof, blocks the synthesis of the specific protein itself. The msDNA system produced in eucaryotic cells to generate a desired complementary DNA of an mRNA of a gene, appears to have real potential in eucaryotic cells to block the expression of various harmful or toxic genes, such as drug resistance, oncogenes, and phages or viruses. The system could have applications to AIDS therapy. Of special interest, are the msDNAs that would be produced by HeLa cells and containing such selected DNA fragment for use in antisense applications.

As described above, it is contemplated that genes be inserted for instance, in the stem region(s) of the msDNAs. Thus the msDNAs may be used for amplification of the selected gene.

The polymerase chain reaction (PCR) is a well-known rapid procedure for in vitro enzymatic amplification of a specific segment of DNA. The standard PCR method requires a segment of double-stranded DNA to be amplified, and always two-single stranded oligonucleotide primers flanking the segment, a DNA polymerase, appropriate deoxyribonucleoside triphosphate (dNTPs), a buffer, and salts (*Current Protocols*, Section 15).

Thus, the msDNAs due to their unique structure (and stability), are expected to be of value in numerous applications in the biochemical, medical, pharmaceutical and other biological sciences.

Further, information relevant to the invention is found in Inouye, "Experimental Manipulation of Gene Expression", Academic Press (1983), Koncz et al., "Methods in Arabidopsis Research", World Scientific Publishing (1992), Guthrie and Fink, "Guide to Yeast Genetics and Molecular Biology", Academic Press (1991), and in the references listed below, each of which is incorporated herein by reference.

A useful reference book is "Genetic Engineering of Plants, An agricultural Perspective", Kosuge et al, Plenum Press (1983), particularly the chapters on Plant Viral Vectors, in vitro Plant Transformation Systems Using Lipsomes and others, which is incorporated herein by reference.

Another useful reference for practical techniques in plant molecular biology is "Methods in Plant Molecular Biology", Schuler and Zielinski, Academic Press (1989), which is incorporated herein by reference. The books techniques are readily applicable to the insertion of the selected retron(s) into plant cells, like leaf discs and culturing cell suspension cultures.

It can be seen that the present invention is providing a significant contribution to arts and science.

While preferred embodiments of the present invention have been described herein, it will be understood that various changes and modifications may be made without departing from the spirit of the invention and these are intended to be within the scope of the claims.

REFERENCES

1. *TIBS*, 16, 18–21 (1991a)
2. *Ann. Rev. Microbiol.*, 45, 163–186 (1991b)
3. Lampson et al., *Progress in Nucleic Acid Research and Molecular Biology*, 60, 1–24
4. *Retroelements*
5. Weiner et al., *Ann. Rev. Biochem.*, 55, 631–661 (1986)
6. Broach et al., *Experimental Manipulation of Gene Expression*, Academic Press Inc., New York, 1983
7. Lampson et al., *Science*, 243, 1033–1038 (1989)
8. Sanger et al., *Proc. Natl. Acad. Sci. USA*, 74, 5463–5467 (1977)
9. Dhundale et al., *Cell*, 51, 1105–1112, 1987
10. Dhundale et al., *J. Biol. Chem.*, 263, 9055–9058, 1988b
11. Furuichi et al., *Cell*, 48, 47–52, 1987a and Furuichi et al., *Cell*, 48, 55–62, 1987b
12. Lim and Maas, *Cell*, 56, 891–904, 1989
13. Sun et al., *J. Bacteriol.*, 173, 4171–4181, 1991
14. Herzer et al., *Mol. Microbiol.*, submitted, August 1991
15. Yanisch-Perron et al., *Gene*, 33, 103–119, 1985
16. Ito et al., *J. Bacteriol.*, 153, 163–168, 1983
17. Kozak, *J. Cell Biology*, 108, 229–241, 1989
18. Boeke et al., *Cell*, 40, 491–500, 1985
19. Hamilton et al., *Nucl. Acids Res.*, 51, 3581–3583, 1987
20. Yee et al., *Cell*, 38, 203–209, 1984
21. Coleman et al., *Cell*, 37, 429–436 (1984)
22. Watson et al., *Molecular Biology of the Gene*, Fourth Ed. (1987), Chapter 18
23. Rose et al., *Methods in Yeast Genetics: A Laboratory Course Manual*, Cold Spring Harbor Lab., Cold Spring Harbor, N.Y., 1990
24. Hoffman and Winston, *Gene*, 57, 268–272, 1987
25. Elder et al., *Proc. Natl. Acad. Sci. USA*, 80, 2432–2436, 1983
26. Chomzynski et al., *Anal. Biochem.*, 162, 156–159, 1987
27. Southern, *Mol. Biol.*, 98, 503–517, 1975
28. Denhardt, *Biochem. Biophys. Res. Commun.*, 23, 641–646 (1966)
29. Rigby et al., *J. Mol. Biol.*, 113, 237–251, 1977
30. *ATCC Catalogue of Yeasts*, 18th Ed., 1990
31. *Genetic Engineering of Plants, An Agricultural Perspective*, Edited by Kosuge et al., Plenum Press (1983)
32. *Methods in Enzymology*, Vol. 194, "Guide to Yeast Genetics and Molecular Biology", page 373 (Guthrie and Fink, Eds., Academic Press Inc., 1991)
33. U.S. Pat. No. 4,415,734
34. Matteuci et al., *J. Am. Chem. Soc.*, 103 (11):3185–3191 (1981)
35. Adams et al., *J. Am. Chem. Soc.*, 105 (3):661–663 (1983)
36. Bemcage et al., *Tetrahedron Letters*, 22 (20):1859–1867 (1981)
37. *Molecular Cloning: A Laboratory Manual*, Second Edition, §3, §16.3 and seq. (Sambrook et al., Cold Spring Harbor Laboratory Press, 1989)
38. *Current Protocols In Molecular Biology*, Volume 1, §16.12–16.13.7 (Ausubel et al., Eds., Greene Publishing Associates and Wiley-Interscience, 1989)
39. *Current Protocols In Molecular Biology*, Volume 1, §9.01–9.93 (Ausubel et al., Eds., Greene Publishing Associates and Wiley-Interscience, 1989)
40. *Science*, 252, 1374–1375 (Jun. 27, 1991), "Triplex DNA Finally Comes of Age"
41. *Current Protocols*, Section 15
42. *Science*, 252, 1643–1650 (Jun. 21, 1991)
43. Ausubel, supra, Unit 9.3
44. *World Scientific Publishing*, Koncz et al 1992, "Methods in Arabidopsis Research".
45. *Academic Press* (1983), "Experimental Manipulation of Gene Expression".
46. *Academic Press* (1991), "Guide to Yeast Genetics and Molecular Biology, Guthrie and Fink.
47. *Genetic Engineering of Plants, An Agricultural Perspective*, Kosuge et al, Plenum Press (1983).

48. *Methods in Plant Molecular Biology,* Schuler and Zielinski, Academic Press (1989).

49. *Gene Expression: General and Cell-Type-Specific,* Karin, Birkhauser Boston (1993).

---

What is claimed is:

1. A eucaryotic cell transfected with a DNA expression vector for replication, which vector contains a retron for msDNA synthesis, which retron contains msr and msd coding regions of the msDNA and a gene encoding a reverse transcriptase.

2. The transfected eucaryotic cell of claim 1 which is a vertebrate or plant cell.

3. The transfected eucaryotic cell of claim 2 which is a vertebrate cell.

4. The transfected eucaryotic vertebrate cell of claim 3 which is a COS, CHO, or HeLa cell.

5. The transfected eucaryotic plant cell of claim 2 which is a monocotyledon or dicotyledon cell.

6. The transfected eucaryotic cell of claim 1 wherein the msDNA contains a foreign nucleic acid fragment.

7. The transfected eucaryotic cell of claim 6 wherein the foreign nucleic acid fragment is in a single stranded portion of the msDNA.

8. The transfected eucaryotic cell of claim 7 wherein the foreign nucleic acid fragment is an antisense fragment.

9. The transfected eucaryotic cell of claim 1 wherein the gene encoding a reverse transcriptase is downstream of the msr and msd coding regions.

10. The transfected eucaryotic cell of claim 1 wherein the gene encoding a reverse transcriptase is upstream of the msr and msd coding regions.

11. An expression vector which contains a retron for msDNA synthesis, which retron contains msr and msd coding regions of the msDNA and a gene encoding a reverse transcriptase.

12. The vector of claim 11 wherein the msDNA contains a foreign nucleic acid fragment.

13. The vector of claim 12 wherein the foreign nucleic acid fragment is in a single stranded portion of the msDNA.

14. The vector of claim 13 wherein the foreign nucleic acid fragment is an antisense fragment.

15. The vector of claim 14 wherein the antisense fragment is 4 to about 100 bases in length.

16. The vector of claim 11 which is selected from the group consisting of YEp521-M1, YEp521-M2, YEp521-M3, YEp521-M4, and YEp521-M5.

17. An msDNA hybrid molecule which comprises a branched single-stranded RNA portion covalently linked to a single-stranded DNA portion by a 2',5'-phosphodiester bond between the 2'-OH group of an internal rG residue and the 5'-phosphate of the DNA molecule, which RNA is non-covalently linked to the DNA by base-pairing between the complementary 3' ends of the RNA and DNA molecules, which msDNA contains a stable stem-loop structure in the RNA and/or the DNA portion of the molecule, and which msDNA contains a foreign nucleic acid fragment.

18. The msDNA of claim 17 wherein the foreign nucleic acid fragment is an antisense fragment.

19. The msDNA of claim 18 wherein the antisense fragment is 4 to 100 bases in length.

20. The msDNA of claim 18 wherein the antisense fragment is a single-stranded fragment complementary to the mRNA of a target gene.

21. The msDNA of claim 17 wherein the foreign nucleic acid fragment is an RNA fragment and is in the single stranded RNA portion of the msDNA.

22. The msDNA of claim 21 wherein the foreign nucleic acid fragment is in the loop of the stem-loop structure of the RNA portion of the msDNA.

23. The msDNA of claim 17 wherein the foreign nucleic acid fragment is a DNA fragment and is in the single stranded DNA portion of the msDNA.

24. The msDNA of claim 23 wherein the foreign nucleic acid fragment is in the loop of the stem-loop structure of the DNA portion of the msDNA.

25. The transfected eucaryotic vertebrate cell of claim 3 which is selected from the group consisting of a fish, bird, and amphibian cell.

26. The transfected eucaryotic vertebrate cell of claim 3 which is a mammalian cell selected from the group consisting of a mouse cell and a human cell.

27. The transfected eucaryotic cell of claim 2 which is plant cell selected from the group consisting of cereals, legumes, grasses, and cotton.

28. The transfected eucaryotic cell of claim 6 which is a plant or vertebrate cell.

29. The transfected eucaryotic plant cell of claim 27 which is selected from the group consisting of a soybean, maize, and pea plant cell.

30. The transfected eucaryotic vertebrate cell of claim 8 which is selected from the group consisting of a mouse and human cell.

* * * * *

UNITED STATES PATENT AND TRADEMARK OFFICE
CERTIFICATE OF CORRECTION

PATENT NO.    : 5,849,563
DATED         : December 15, 1998
INVENTOR(S)   : Miyata et al.

It is certified that error appears in the above-identified patent and that said Letters Patent is hereby corrected as shown below:

Column 1,
Line 15, before FIELD OF THE INVENTION, please insert the following paragraph:

-- The U.S. Government has a paid-up license in this invention and the right in limited circumstances to require the patent owner to license others on reasonable terms as provided for by the terms of Grant Nos. GM26843 and GM44012 awarded by the NIH. --

Signed and Sealed this

Fifteenth Day of July, 2003

JAMES E. ROGAN
*Director of the United States Patent and Trademark Office*

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCAAGCTTCA TAAACACGCA TGT                                          23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTGGATCCAG AAACGCATGC AGG                                          23

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTGGATCCAA GAAATGACAA AAACA                                      25

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTGGATCCTT CATTAGCTAT TTAACAT                                    27

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTCTCCATGG TTAAAACATC TAAACTT                                    27

( 2 ) INFORMATION FOR SEQ ID NO:6:

( i ) SEQUENCE CHARACTERISTICS:
        ( A ) LENGTH: 24 base pairs (B) TYPE: nucleic acid
(C) STRANDEDNESS: single
(D) TOPOLOGY: linear (xi) SEQUENCE DESCRIPTION: SEQ ID NO:6:

TAAAGCTTTC AAAAAAATCC TTAA     24

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:7:

TTTCATTATT AATACCCTCT AGATT     25

(2) INFORMATION FOR SEQ ID NO:8:

(i) SEQUENCE CHARACTERISTICS:
(A) LENGTH: 162 base pairs
(B) TYPE: nucleic acid
(C) STRANDEDNESS: single
(D) TOPOLOGY: linear (ix) FEATURE:
(A) NAME/KEY: misc_feature
(B) LOCATION: 1
(D) OTHER INFORMATION: /note= "The 5'position of this
nucleotide is linked to the 2'position of
nucleotide number 20 of SEQ ID NO: 9 of this
application."

(ix) FEATURE:
(A) NAME/KEY: misc_binding
(B) LOCATION: 155..162
(D) OTHER INFORMATION: /note= "This region can hydrogen
bond to nucleotides 70-77 of SEQ ID NO: 9 of this
application."

(xi) SEQUENCE DESCRIPTION: SEQ ID NO:8:

CATCTTACCT GGGGCACGGT AGCCTCACCG GCTCTCCCCT CCTAGGCACT ACGGCCGGGG     60

TGGGTAAACG GCGGTCGCGT CGTTGGCTCC GCTACCCACC CTGGCCGTAG TGCCTAGGAG     120

GGAGAGAGCC AAGAACAGGC TACCTTGCGG AGAGTGTCCT GC     162

(2) INFORMATION FOR SEQ ID NO:9:

(i) SEQUENCE CHARACTERISTICS:
(A) LENGTH: 77 base pairs
(B) TYPE: nucleic acid
(C) STRANDEDNESS: single
(D) TOPOLOGY: linear (ix) FEATURE:
(A) NAME/KEY: misc_feature
(B) LOCATION: 20
(D) OTHER INFORMATION: /note= "The 2'position of this
nucleotide is linked to the 5'position of
nucleotide number 1 of SEQ ID NO: 8 of this
application."

(ix) FEATURE:
(A) NAME/KEY: misc_binding
(B) LOCATION: 70..77
(D) OTHER INFORMATION: /note= "This region can hydrogen
bond to nucleotides 155-162 of SEQ ID NO: 8 of
this application."

(xi) SEQUENCE DESCRIPTION: SEQ ID NO:9:

AGAGGUCCGG AGUGCAUCAG CCUGAGCGCC UCGAGCGGCG GAGCGGCGUU GCGCCGCUCC     60

GGUUGGAAUG CAGGACA 77

( 2 ) INFORMATION FOR SEQ ID NO:10:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note= "The 5'position of this nucleotide is linked to the 2'position of nucleotide number 4 of SEQ ID NO: 11 of this application."

( i x ) FEATURE:
        ( A ) NAME/KEY: misc_binding
        ( B ) LOCATION: 60..65
        ( D ) OTHER INFORMATION: /note= "This region can hydrogen bond to nucleotides 44-49 of SEQ ID NO: 11 of this application."

( x i ) SEQUENCE DESCRIPTION: SEQ ID NO:10:

CTGCGAGGCG TTGGACCCGG GGCTCCCTGC GTTGCGTACG CTGGGACCCT GGCGAAGAGA 60

TGGGG 65

( 2 ) INFORMATION FOR SEQ ID NO:11:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 4
        ( D ) OTHER INFORMATION: /note= "The 2'position of this nucleotide is linked to the 5'position of nucleotide number 1 of SEQ ID NO: 10 of this application."

( i x ) FEATURE:
        ( A ) NAME/KEY: misc_binding
        ( B ) LOCATION: 44..49
        ( D ) OTHER INFORMATION: /note= "This region can hydrogen bond to nucleotides 60-65 of SEQ ID NO: 10 of this application."

( x i ) SEQUENCE DESCRIPTION: SEQ ID NO:11:

UGAGCCAUGA GUACCGCGGU GUUUCGCCGC GGGGGUGUUC UGUCCCAU 49

( 2 ) INFORMATION FOR SEQ ID NO:12:

( i ) SEQUENCE CHARACTERISTICS:
        ( A ) LENGTH: 163 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note= "The 5'position of this nucleotide is linked to the 2'position of nucleotide number 19 of SEQ ID NO: 13 of this application."

( i x ) FEATURE:
        ( A ) NAME/KEY: misc_binding (B) LOCATION: 156..163
(D) OTHER INFORMATION: /note= "This region can hydrogen bond to nucleotides 69-76 of SEQ ID NO: 13 of this application."

(xi) SEQUENCE DESCRIPTION: SEQ ID NO:12:

| | | | | | |
|---|---|---|---|---|---|
| CTTCTCACCT | GGGGCACGGT | AGCCTCACCG | GCTCTCCCCT | CCGGTGAGTA | CCTCTCCGGC | 60 |
| CGGGGAAACG | GCGGTTGCGT | CGTTGGTTCA | GCTCCCCGGC | CGGAGAGGTA | CTCACCGGAG | 120 |
| GGAAGAGAGC | CAAGAACAGG | CTACCTTGCG | GAGAGTGTCC | TGC | | 163 |

(2) INFORMATION FOR SEQ ID NO:13:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 19
        (D) OTHER INFORMATION: /note= "The 2'position of this nucleotide is linked to the 5'position of nucleotide number 1 of SEQ ID NO: 12 of this application."

(ix) FEATURE:
        (A) NAME/KEY: misc_binding
        (B) LOCATION: 69..76
        (D) OTHER INFORMATION: /note= "This region can hydrogen bond to nucleotides 156-163 of SEQ ID NO: 12 of this application."

(xi) SEQUENCE DESCRIPTION: SEQ ID NO:13:

| | | | | | |
|---|---|---|---|---|---|
| AGAGGUCCCA | AGCCAUCAGC | CUCAGCGCCU | CGAGCGCGAG | AGCGGCGUUG | CGCCGCUCUG | 60 |
| GUUGAAUUGC | AGGACA | | | | | 76 |

(2) INFORMATION FOR SEQ ID NO:14:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "The 5'position of this nucleotide is linked to the 2'position of nucleotide number 18 of SEQ ID NO:15 of this application."

(ix) FEATURE:
        (A) NAME/KEY: misc_binding
        (B) LOCATION: 102..107
        (D) OTHER INFORMATION: /note= "This region can hydrogen bond to nucleotides 70-75 of SEQ ID NO: 15 of this application."

(xi) SEQUENCE DESCRIPTION: SEQ ID NO:14:

| | | | | | |
|---|---|---|---|---|---|
| CATTAAACCA | TCCCGAAGGC | GCGTAACTGT | ACTGAGCGCG | TCAGCGCGAC | GTACGCGAAG | 60 |
| CGTACTCAGG | TACAAATGAG | CGAGTTTGGG | TATATGGACA | TACTACT | | 107 |

(2) INFORMATION FOR SEQ ID NO:15:

(i) SEQUENCE CHARACTERISTICS:
        (A) LENGTH: 75 base pairs
        (B) TYPE: nucleic acid
        (C) STRANDEDNESS: single (D) TOPOLOGY: linear (ix) FEATURE:
    (A) NAME/KEY: misc_feature
    (B) LOCATION: 18
    (D) OTHER INFORMATION: /note= "The 2'position of this
        nucleotide is linked to the 5'position of
        nucleotide number 1 of SEQ ID NO: 14 of this
        application."

(ix) FEATURE:
    (A) NAME/KEY: misc_binding
    (B) LOCATION: 70..75
    (D) OTHER INFORMATION: /note= "This region can hydrogen
        bond to nucleotides 102-107 of SEQ ID NO: 14 of
        this application."

(xi) SEQUENCE DESCRIPTION: SEQ ID NO:15:

CGCCAGCAGU GGCAAUAGCG UUUCCGGCCU UUUGUGCCGG GAGGGUCGGC GAGUCGCUGA 60

CUUAACGCCA GUAGU 75

(2) INFORMATION FOR SEQ ID NO:16:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "The 5'position of this
            nucleotide is linked to the 2'position of
            nucleotide number 15 of SEQ ID NO: 17 of this
            application."

(ix) FEATURE:
        (A) NAME/KEY: misc_binding
        (B) LOCATION: 61..67
        (D) OTHER INFORMATION: /note= "This region can hydrogen
            bond to nucleotides 52-58 of SEQ ID NO: 17 of this
            application."

(xi) SEQUENCE DESCRIPTION: SEQ ID NO:16:

TCCTTCGCAC AGCACACCTG CCGTATAGCT CTGAATCAAG GATTTAGGG AGGCGATTCC 60

TCCTGCC 67

(2) INFORMATION FOR SEQ ID NO:17:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 15
        (D) OTHER INFORMATION: /note= "The 2'position of this
            nucleotide is linked to the 5'position of
            nucleotide number 1 of SEQ ID NO: 16 of this
            application."

(ix) FEATURE:
        (A) NAME/KEY: misc_binding
        (B) LOCATION: 52..58
        (D) OTHER INFORMATION: /note= "This region can hydrogen
            bond to nucleotides 61-67 of SEQ ID NO: 16 of this
            application."

(xi) SEQUENCE DESCRIPTION: SEQ ID NO:17:

CACGCAUGUA GGCAGAUUUG UUGGUUGUGA AUCGCAACCA GUGGCCUUAA UGGCAGGA 58

( 2 ) INFORMATION FOR SEQ ID NO:18:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note= "The 5'position of this
            nucleotide is linked to the 2'position of
            nucleotide number 14 of SEQ ID NO: 19 of this
            application."

( i x ) FEATURE:
        ( A ) NAME/KEY: misc_binding
        ( B ) LOCATION: 76..86
        ( D ) OTHER INFORMATION: /note= "This region can hydrogen
            bond to nucleotides 72-82 of SEQ ID NO: 19 of this
            application."

( x i ) SEQUENCE DESCRIPTION: SEQ ID NO:18:

```
GTCAGAAAAA   ACGGGTTTCC   TGGTTGGCTC   GGAGAGCATC   AGGCGATGCT   CTCCGTTCCA      60

ACAAGGAAAA   CAGACAGTAA   CTCAGA                                                 86
```

( 2 ) INFORMATION FOR SEQ ID NO:19:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 14
        ( D ) OTHER INFORMATION: /note= "The 2'position of this
            nucleotide is linked to the 5'position of
            nucleotide number 1 of SEQ ID NO: 18 of this
            application."

( i x ) FEATURE:
        ( A ) NAME/KEY: misc_binding
        ( B ) LOCATION: 72..82
        ( D ) OTHER INFORMATION: /note= "This region can hydrogen
            bond to nucleotides 76-86 of SEQ ID NO: 18 of this
            application."

( x i ) SEQUENCE DESCRIPTION: SEQ ID NO:19:

```
AUGCGCACCC   UUAGCGAGAG   GUUUAUCAUU   AAGGUCAACC   UCUGGAUGUU   GUUUCGGCAU      60

CCUGCAUUGA   AUCUGAGUUA   CU                                                     82
```

( 2 ) INFORMATION FOR SEQ ID NO:20:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note= "The 5'position of this
            nucleotide is linked to the 2'position of
            nucleotide number 15 of SEQ ID NO: 21 of this
            application."

( i x ) FEATURE:
        ( A ) NAME/KEY: misc_binding (B) LOCATION: 69..73
(D) OTHER INFORMATION: /note= "This region can hydrogen bond to nucleotides 71-75 of SEQ ID NO: 21 of this application."

(x i) SEQUENCE DESCRIPTION: SEQ ID NO:20:

TTGAGCACGT CGATCAGTTC GCTGATCGGT GGCCCCAGC CGCCGCTCAG CGAACTGAAC 60

GACGGGCATA GCT 73

(2) INFORMATION FOR SEQ ID NO:21:

(i) SEQUENCE CHARACTERISTICS:
(A) LENGTH: 75 base pairs
(B) TYPE: nucleic acid
(C) STRANDEDNESS: single
(D) TOPOLOGY: linear (ix) FEATURE:
(A) NAME/KEY: misc_feature
(B) LOCATION: 15
(D) OTHER INFORMATION: /note= "The 2'position of this nucleotide is linked to the 5'position of nucleotide number 1 of SEQ ID NO: 20 of this application."

(ix) FEATURE:
(A) NAME/KEY: misc_binding
(B) LOCATION: 71..75
(D) OTHER INFORMATION: /note= "This region can hydrogen bond to nucleotides 69-73 of SEQ ID NO: 20 of this application."

(x i) SEQUENCE DESCRIPTION: SEQ ID NO:21:

CAGAGCCAAA CCUAGCAUUU UAUGGGUUAA UAGCCCAUCG CGCAUGAGUC AUGGUUUCGC 60

CUAGUAUUUU AGCUA 75

(2) INFORMATION FOR SEQ ID NO:22:

(i) SEQUENCE CHARACTERISTICS:
(A) LENGTH: 67 base pairs
(B) TYPE: nucleic acid
(C) STRANDEDNESS: single
(D) TOPOLOGY: linear (ix) FEATURE:
(A) NAME/KEY: misc_feature
(B) LOCATION: 1
(D) OTHER INFORMATION: /note= "The 5'position of this nucleotide is linked to the 2'position of nucleotide number 15 of SEQ ID NO: 23 of this application."

(ix) FEATURE:
(A) NAME/KEY: misc_binding
(B) LOCATION: 61..67
(D) OTHER INFORMATION: /note= "This region can hydrogen bond to nucleotides 52-58 of SEQ ID NO: 23 of this application."

(x i) SEQUENCE DESCRIPTION: SEQ ID NO:22:

TCCTTCGCAC AGCACACCTG CCGTATAGCT CTGAATCAAG GATTTAGGG AGGCGATTCC 60

TCCTGCC 67

(2) INFORMATION FOR SEQ ID NO:23:

(i) SEQUENCE CHARACTERISTICS:
(A) LENGTH: 58 base pairs
(B) TYPE: nucleic acid
(C) STRANDEDNESS: single
(D) TOPOLOGY: linear -continued (ix) FEATURE:
 (A) NAME/KEY: misc_feature
 (B) LOCATION: 15
 (D) OTHER INFORMATION: /note= "The 2'position of this
  nucleotide is linked to the 5'position of
  nucleotide number 1 of SEQ ID NO: 22 of this
  application."

(ix) FEATURE:
 (A) NAME/KEY: misc_binding
 (B) LOCATION: 52..58
 (D) OTHER INFORMATION: /note= "This region can hydrogen
  bond to nucleotides 61-67 of SEQ ID NO: 22 of this
  application."

(xi) SEQUENCE DESCRIPTION: SEQ ID NO:23:

CACGCAUGUA GGCAGAUUUG UUGGUUGUGA AUCGCAACCA GUGGCCUUAA UGGCAGGA    58

(2) INFORMATION FOR SEQ ID NO:24:

(i) SEQUENCE CHARACTERISTICS:
  (A) LENGTH: 58 base pairs
  (B) TYPE: nucleic acid
  (C) STRANDEDNESS: double
  (D) TOPOLOGY: linear (xi) SEQUENCE DESCRIPTION: SEQ ID NO:24:

TCGATGTAAT TTGCTAATTC ACCGCTCATG TTCGAAGGAT AGTTCTATTT GATCTCGA    58